(12) United States Patent
Gao et al.

(10) Patent No.: US 9,310,375 B2
(45) Date of Patent: Apr. 12, 2016

(54) LUMINOPHORE-LABELED MOLECULES COUPLED WITH PARTICLES FOR MICROARRAY-BASED ASSAYS

(75) Inventors: Huafang Gao, Beijing (CN); Guangxin Xiang, Beijing (CN); Di Jiang, Beijing (CN); Wanli Xing, Beijing (CN); Jing Cheng, Beijing (CN)

(73) Assignees: CapitalBio Corporation, Beijing (CN); Tsinghua University, Beijing (CN)

( * ) Notice: Subject to any disclaimer, the term of this patent is extended or adjusted under 35 U.S.C. 154(b) by 39 days.

(21) Appl. No.: 13/877,320

(22) PCT Filed: Oct. 27, 2010

(86) PCT No.: PCT/CN2010/001711
§ 371 (c)(1),
(2), (4) Date: Jun. 12, 2013

(87) PCT Pub. No.: WO2012/055069
PCT Pub. Date: Mar. 5, 2012

(65) Prior Publication Data
US 2013/0267436 A1  Oct. 10, 2013

(51) Int. Cl.
*G01N 33/58* (2006.01)
*C12Q 1/68* (2006.01)
(Continued)

(52) U.S. Cl.
CPC ............ *G01N 33/582* (2013.01); *C12Q 1/6816* (2013.01); *C12Q 1/6837* (2013.01);
(Continued)

(58) Field of Classification Search
CPC . G01N 33/582; G01N 33/543; C12Q 1/6883; C12Q 1/6816; C12Q 1/6827; C12Q 1/6837; C40B 30/04; C40B 40/00; C40B 40/06; C40B 40/10; C40B 40/12

USPC .............. 506/9, 13, 16, 18, 19; 435/6.1, 6.11, 435/6.12; 536/24.33
See application file for complete search history.

(56) References Cited

U.S. PATENT DOCUMENTS

| 4,683,195 A | 7/1987 | Mullis et al. |
| 4,683,202 A | 7/1987 | Mullis |

(Continued)

FOREIGN PATENT DOCUMENTS

| CN | 1643379 | 7/2005 |
| CN | 1699595 | 11/2005 |

(Continued)

OTHER PUBLICATIONS

Extended European Search Report issued for EP10858798.1, dated Feb. 10, 2014, 8 pages.
(Continued)

*Primary Examiner* — Samuel Woolwine
*Assistant Examiner* — Kaijiang Zhang
(74) *Attorney, Agent, or Firm* — Morrison & Foerster LLP

(57) ABSTRACT

A microarray-based assay is provided, which is used for analyzing molecular interactions, including polynucleotides, polypeptides, antibodies, small molecule compounds, peptides and carbohydrates. Such method comprises labeling a target molecule with a luminophore, coupling the target molecule to a particle, and binding to a probe molecule on microarray. In particular, multiplexed genetic analysis of nucleic acid fragments can be implemented. Specific genes, single nucleotide polymorphisms or gene mutations, such as deletions, insertions, and indels, can be identified. This technology, with high sensitivity, enables the detection and interpretation of molecular interactions in an efficient way.

27 Claims, 6 Drawing Sheets

(51) Int. Cl.
*C40B 30/04* (2006.01)
*G01N 33/543* (2006.01)

(52) U.S. Cl.
CPC .............. *C12Q1/6883* (2013.01); *C40B 30/04* (2013.01); *G01N 33/54333* (2013.01); *G01N 33/54386* (2013.01); *C12Q 2600/156* (2013.01); *C12Q 2600/158* (2013.01); *C12Q 2600/16* (2013.01)

(56) References Cited

U.S. PATENT DOCUMENTS

| | | | |
|---|---|---|---|
| 4,889,818 | A | 12/1989 | Gelfand et al. |
| 4,965,188 | A | 10/1990 | Mullis et al. |
| 5,656,493 | A | 8/1997 | Mullis et al. |
| 5,681,702 | A | 10/1997 | Collins et al. |
| 5,780,610 | A | 7/1998 | Collins et al. |
| 5,998,143 | A | 12/1999 | Ellis et al. |
| 6,077,664 | A | 6/2000 | Slater et al. |
| 6,140,054 | A | 10/2000 | Wittwer et al. |
| 2005/0147974 | A1 | 7/2005 | Muller-Shulte |
| 2007/0269817 | A1 | 11/2007 | Shapero |
| 2010/0041563 | A1 | 2/2010 | Li et al. |
| 2010/0151443 | A1 | 6/2010 | Xiang et al. |

FOREIGN PATENT DOCUMENTS

| | | |
|---|---|---|
| CN | 101680893 | 3/2010 |
| WO | WO-00/58516 | 10/2000 |
| WO | WO-01/27327 | 4/2001 |
| WO | WO-01/27329 | 4/2001 |
| WO | WO-02/068684 | 9/2002 |
| WO | WO-2007/092538 | 8/2007 |

OTHER PUBLICATIONS

Fan et al., "Highly parallel genomic assays," Nat Rev Genet (2006) 7(8):632-644.
Gao et al., "Comparison of different methods for preparing single stranded DNA for oligonucleotide microarray," Anal Letters (2003) 33(13):2849-2863.
Gerry et al., "Universal DNA microarray method for multiplex detection of low abundance point mutations," J Mol Biol (1999) 292:251-262.
Heller, "DNA microarray technology: devices, systems, and applications," Ann Rev Biomed Eng (2002) 4:129-153.
Hoheisel, "Microarray technology: beyond transcript profiling and genotype analysis," Nat Rev Genet (2006) 7:200-210.
International Preliminary Report on Patentability and Written Opinion issued for PCT/CN2010/001711, issued Apr. 30, 2013, 6 pages.
International Search Report issued for PCT/CN2010/001711, mailed Aug. 11, 2011, 5 pages.
Kanehisa, "Use of statistical criteria for screening potential homologies in nucleic acid sequences," Nucleic Acids Res (1984) 12:203-213.
Kurt et al., "Multiplexed genotyping of methicillin-resistant *Staphylococcus aureus* isolates by use of padlock probes and tag microarrays," J Clin Microbiol (2009) 47(3):577-585.
Leach et al., "Theoretical investigations of novel nucleic acid base," J Am Chem Soc (1992) 114:3675-3683.
Li et al., "Construction of a multiplex allele-specific PCR-based universal array (ASPUA) and its application to hearing loss screening," Hum Mutat (2008) 29:306-314.
Liu et al., "An integrated and sensitive detection platform for biosensing application based on Fe@Au magnetic nanoparticles as bead array carries," Biosens Bioelectron (2010) 26(4):1442-1448.
Mantsch et al., "Structural and enzymatic properties of adenine 1-oxide nucleotides," Biochemistry (1975) 14(26):5593-5601.
Marshall and Hodgson, "DNA chips: an array of possibilities," Nat Biotechnol (1998) 16:27-31.
Matson et al., "Biopolymer synthesis on polypropylene supports: oligonucleotide arrays," Anal Biochem (1995) 224(1):110-116.
Matteucci and Caruthers, "Synthesis of deoxyoligonucleotides on a polymer support," J Am Chem Soc (1981) 103:3185-3191.
Milligan et al., "Current concepts in antisense drug design," J Med Chem (1993) 36:1923-1937.
Mulvaney et al., "Direct detection of genomic DNA with fluidic force discrimination assays," Anal Biochem (2009) 392:139-144.
Piccirilli et al., "Enzymatic incorporation of a new base pair into DNA and RNA extends the genetic alphabet," Nature (1990) 343:33-37.
Ramsay, "DNA chips: state-of-the art," Nat Biotechnol (1998) 16:40-44.
Riccelli et al., "Hybridization of single-stranded DNA targets to immobilized complementary DNA probes: comparison of hairpin versus linear capture probes," Nucleic Acids Res (2001) 29:996-1004.
Rodriguez-Paris et al., "Genotyping with a 198 mutation arrayed primer extension array for hereditary hearing loss: assessment of its diagnostic value for medical practice," PLOs One (2010) 5(7):e11804, 7 pages.
Sassolas et al., "DNA biosensors and microarrays," Chem Rev (2008) 108:109-139.
Schena et al., "Parallel human genome analysis: Microarray-based expression monitoring of 1000 genes," Proc Natl Acad Sci USA (1996) 93:10614-10619.
Shaw et al., "Modified deoxyoligonucleotides stable to exonuclease degradation in serum," Nucleic Acids Res (1991) 19:747-750.
Shlyapnikov et al., "Detection of microarray-hybridized oligonucleotides with magnetic beads," Anal Biochem (2010) 399:125-131.
Stoughton, "Applications of DNA microarrays in biology," Ann Rev Biochem (2005) 74:53-82.
Switzer et al., "Enzymatic recognition of the base pair between isocytidine and isoguanosine," Biochemistry (1993) 32:10489-10496.
Xu and Lam, "Protein and chemical microarrays—powerful tools for proteomics," J Biomed Biotechnol (2003) 5:257-266.
Tor and Dervan, Site-specific enzymic incorporation of an unnatural base, N6-(6-aminohexyl)isoguanosine, into RNA, J Am Chem Soc (1993) 115:4461-4467.
Zhu et al., "Multiplex asymmetric PCR-based oligonucleotide microarray for detection of drug resistance genes containing single mutations in Enterobacteriaceae," Antimicrob Agents Chemother (2007) 51:3707-3713.
Zhao et al., "Maternally Inherited Aminoglycoside-Induced and Non syndromic Deafness Is Associated with the Novel C1494T Mutation in the Mitochondrial 12S rRNA Gene in a Large Chinese Family," The American Journal of Human Genetics (2004) 74:139-152.
Response to Communication pursuant to Rules 70(2) and 70a(2) EPC for EP 10 858 798.1, filed Sep. 4, 2014, 12 pages.
Notice of Reasons for Rejection (translation) for JP 2013-535229, mailed Dec. 17, 2014, 6 pages.

SEQUENCE LISTING

<160> NUMBER OF SEQ ID NOS: 46

<210> SEQ ID NO 1
<211> LENGTH: 37
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature
<222> LOCATION: 1
<223> OTHER INFORMATION: modified by an amino group NH2

<400> SEQUENCE: 1
tttttttttt tttttgagga gatcgtagct ggtgcat                37

<210> SEQ ID NO 2
<211> LENGTH: 37
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature
<222> LOCATION: 1
<223> OTHER INFORMATION: modified by an amino group NH2

<400> SEQUENCE: 2
tttttttttt tttttcgct gccaaccgag aattgca                                37

<210> SEQ ID NO 3
<211> LENGTH: 37
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature
<222> LOCATION: 1
<223> OTHER INFORMATION: modified by an amino group NH2

<400> SEQUENCE: 3
tttttttttt tttttgagca agcgcaaacg cagtact                               37

<210> SEQ ID NO 4
<211> LENGTH: 37
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature
<222> LOCATION: 1
<223> OTHER INFORMATION: modified by an amino group NH2

<400> SEQUENCE: 4
tttttttttt tttttgcata gacgtggctc aactgtc                               37

<210> SEQ ID NO 5
<211> LENGTH: 39
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature
<222> LOCATION: 1
<223> OTHER INFORMATION: modified by an amino group NH2

<400> SEQUENCE: 5
tttttttttt tttttcaagg cacgtcccag acgcatcaa                             39

<210> SEQ ID NO 6
<211> LENGTH: 38
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature
<222> LOCATION: 1
<223> OTHER INFORMATION: modified by an amino group NH2

<400> SEQUENCE: 6
tttttttttt tttttcggc acgcgcgaga tcaccatc                               38

<210> SEQ ID NO 7
<211> LENGTH: 39
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature
<222> LOCATION: 1

<223> OTHER INFORMATION: modified by an amino group NH2

<400> SEQUENCE: 7
tttttttttt tttttttttc ccgtccgtca tcgctcaag                              39

<210> SEQ ID NO 8
<211> LENGTH: 39
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature
<222> LOCATION: 1
<223> OTHER INFORMATION: modified by an amino group NH2

<400> SEQUENCE: 8
tttttttttt tttttggtat cgcgaccgca tcccaatct                              39

<210> SEQ ID NO 9
<211> LENGTH: 39
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature
<222> LOCATION: 1
<223> OTHER INFORMATION: modified by an amino group NH2

<400> SEQUENCE: 9
tttttttttt ttttttccct gtctcgttgc gtgtctcgt                              39

<210> SEQ ID NO 10
<211> LENGTH: 38
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature
<222> LOCATION: 1
<223> OTHER INFORMATION: modified by an amino group NH2

<400> SEQUENCE: 10
tttttttttt tttttgttag ggtcgcgcca aactctcc                               38

<210> SEQ ID NO 11
<211> LENGTH: 37
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature
<222> LOCATION: 1
<223> OTHER INFORMATION: modified by an amino group NH2

<400> SEQUENCE: 11
tttttttttt tttttagcta gaccactcag cagactg                                37

<210> SEQ ID NO 12
<211> LENGTH: 37
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature

```
<222> LOCATION: 1
<223> OTHER INFORMATION: modified by an amino group NH2

<400> SEQUENCE: 12 ttttttttttt tttttcgcct tagacagctt gctcatg                              37

<210> SEQ ID NO 13
<211> LENGTH: 38
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature
<222> LOCATION: 1
<223> OTHER INFORMATION: modified by an amino group NH2

<400> SEQUENCE: 13 ttttttttttt tttttaccctt tcgcttcacc ggccgatc                             38

<210> SEQ ID NO 14
<211> LENGTH: 38
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature
<222> LOCATION: 1
<223> OTHER INFORMATION: modified by an amino group NH2

<400> SEQUENCE: 14 ttttttttttt tttttgctcg aagaggcgct acagatcc                              38

<210> SEQ ID NO 15
<211> LENGTH: 37
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature
<222> LOCATION: 1
<223> OTHER INFORMATION: modified by an amino group NH2

<400> SEQUENCE: 15 ttttttttttt tttttctgtt aaacgtcaga gcgcagc                               37

<210> SEQ ID NO 16
<211> LENGTH: 37
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature
<222> LOCATION: 1
<223> OTHER INFORMATION: modified by an amino group NH2

<400> SEQUENCE: 16 ttttttttttt tttttagtcg aagtgtgcgt cagactc                               37

<210> SEQ ID NO 17
<211> LENGTH: 32
<212> TYPE: DNA
<213> ORGANISM: Artificial Sequence
<220> FEATURE:
<223> OTHER INFORMATION: synthetically constructed probe
<220> FEATURE:
```

```
<221> NAME/KEY: misc_feature
<222> LOCATION: 1
<223> OTHER INFORMATION: modified by an amino group NH2
<220> FEATURE:
<221> NAME/KEY: misc_feature
<222> LOCATION: 32
<223> OTHER INFORMATION: biotinylated

<400> SEQUENCE: 17 ttttttttttt tttttgcaac caccaccgga gg                                   32

<210> SEQ ID NO 18
<211> LENGTH: 37
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature
<222> LOCATION: 1
<223> OTHER INFORMATION: modified by an amino group NH2

<400> SEQUENCE: 18 ttttttttttt tttttgcac gagttgggtg agtttgg                               37

<210> SEQ ID NO 19
<211> LENGTH: 38
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature
<222> LOCATION: 1
<223> OTHER INFORMATION: modified by an amino group NH2

<400> SEQUENCE: 19 ttttttttttt ttttgctttt atccctaacg tcatcggg                             38

<210> SEQ ID NO 20
<211> LENGTH: 36
<212> TYPE: DNA
<213> ORGANISM: Artificial Sequence
<220> FEATURE:
<223> OTHER INFORMATION: synthetically constructed probe
<220> FEATURE:
<221> NAME/KEY: misc_feature
<222> LOCATION: 1
<223> OTHER INFORMATION: modified by an amino group NH2

<400> SEQUENCE: 20 ttttttttttt ttttcagag tgcttggtgc cataac                                36

<210> SEQ ID NO 21
<211> LENGTH: 56
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: modified by an amino group NH2

<400> SEQUENCE: 21 ttttttttttt ttttaggag atcgtagctg gtgcattgtt tgttcacacc cccgag          56

<210> SEQ ID NO 22
<211> LENGTH: 56
```

```
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: modified by an amino group NH2

<400> SEQUENCE: 22 ttttttttttt tttttcgct gccaaccgag aattgcatgt ttgttcacac ccgcag        56

<210> SEQ ID NO 23
<211> LENGTH: 16
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: biotinylated

<400> SEQUENCE: 23
gcttgcttac ccagac                                                    16

<210> SEQ ID NO 24
<211> LENGTH: 57
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: modified by an amino group NH2

<400> SEQUENCE: 24 ttttttttttt tttttgagca agcgcaaacg cagtactcca ggctgcaaga acgtgtg      57

<210> SEQ ID NO 25
<211> LENGTH: 55
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: modified by an amino group NH2

<400> SEQUENCE: 25 ttttttttttt tttttgcata gacgtggctc aactgtcacc ctgcagccag ctacg        55

<210> SEQ ID NO 26
<211> LENGTH: 18
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: biotinylated

<400> SEQUENCE: 26
gagccttcga tgcggacc                                                  18

<210> SEQ ID NO 27
```

```
<211> LENGTH: 57
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: modified by an amino group NH2

<400> SEQUENCE: 27
tttttttttt tttttcaagg cacgtcccag acgcatcaaa aacggctatg ggccctg      57

<210> SEQ ID NO 28
<211> LENGTH: 55
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: modified by an amino group NH2

<400> SEQUENCE: 28
tttttttttt tttttcggc acgcgcgaga tcaccatcat ccggctatgg gcctg          55

<210> SEQ ID NO 29
<211> LENGTH: 18
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: biotinylated

<400> SEQUENCE: 29
gagccttcga tgcggacc                                                  18

<210> SEQ ID NO 30
<211> LENGTH: 58
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: modified by an amino group NH2

<400> SEQUENCE: 30
tttttttttt ttttttttc ccgtccgtca tcgctcaagt ggcctaccgg agacatga      58

<210> SEQ ID NO 31
<211> LENGTH: 58
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: modified by an amino group NH2

<400> SEQUENCE: 31
tttttttttt ttttggtat cgcgaccgca tcccaatctc gtggcctacc ggagacga      58
```

```
<210> SEQ ID NO 32
<211> LENGTH: 18
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: biotinylated

<400> SEQUENCE: 32
gagccttcga tgcggacc                                                 18

<210> SEQ ID NO 33
<211> LENGTH: 62
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: modified by an amino group NH2

<400> SEQUENCE: 33
tttttttttt tttttccct gtctcgttgc gtgtctcgtg acacattctt tatgacggtc     60
ca                                                                  62

<210> SEQ ID NO 34
<211> LENGTH: 58
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: modified by an amino group NH2

<400> SEQUENCE: 34
tttttttttt ttttgttag ggtcgcgcca aactctccac attcttttg tcggtccg        58

<210> SEQ ID NO 35
<211> LENGTH: 22
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: biotinylated

<400> SEQUENCE: 35
caaggttttc cagattgctg ag                                            22

<210> SEQ ID NO 36
<211> LENGTH: 60
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: modified by an amino group NH2

<400> SEQUENCE: 36
```
tttttttttt ttttagcta gaccactcag cagactgaat ggcagtagca attatcgact    60

<210> SEQ ID NO 37
<211> LENGTH: 58
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: modified by an amino group NH2

<400> SEQUENCE: 37
tttttttttt ttttcgcct tagacagctt gctcatgtgg cagtagcaat tatcgtgc    58

<210> SEQ ID NO 38
<211> LENGTH: 20
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: biotinylated

<400> SEQUENCE: 38
cgtgtagcag caggaagtat    20

<210> SEQ ID NO 39
<211> LENGTH: 61
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: modified by an amino group NH2

<400> SEQUENCE: 39
tttttttttt ttttaccttt tcgcttcacc ggccgatcct ttgaaagtat acttgaggag    60
g    61

<210> SEQ ID NO 40
<211> LENGTH: 60
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: modified by an amino group NH2

<400> SEQUENCE: 40
tttttttttt ttttgctcg aagaggcgct acagatccct ttgaagtata cttgaggaga    60

<210> SEQ ID NO 41
<211> LENGTH: 20
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: biotinylated

<400> SEQUENCE: 41
ccctgatgaa ggctacaaag                                               20

<210> SEQ ID NO 42
<211> LENGTH: 58
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: modified by an amino group NH2

<400> SEQUENCE: 42
tttttttttt tttttctgtt aaacgtcaga gcgcagcact taccatgtta cgactagt    58

<210> SEQ ID NO 43
<211> LENGTH: 59
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: modified by an amino group NH2

<400> SEQUENCE: 43
tttttttttt tttttagtcg aagtgtgcgt cagactccac ttaccatgtt acgactcgc   59

<210> SEQ ID NO 44
<211> LENGTH: 20
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: biotinylated

<400> SEQUENCE: 44
ccctgatgaa ggctacaaag                                               20

<210> SEQ ID NO 45
<211> LENGTH: 56
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1
<223> OTHER INFORMATION: modified by an amino group NH2

<400> SEQUENCE: 45
tttttttttt tttttgcac gagttgggtg agtttgggtg gactgctaca ttggcc       56

<210> SEQ ID NO 46
<211> LENGTH: 19
<212> TYPE: DNA
<213> ORGANISM: Artificial Sequence
<220> FEATURE:
<223> OTHER INFORMATION: synthetically constructed primer
<220> FEATURE:
<221> NAME/KEY: misc_feature
<222> LOCATION: 1

-continued

```
<223> OTHER INFORMATION: biotinylated

<400> SEQUENCE: 46
tcgaggcttg tccttgtgc                                                   19
```

LUMINOPHORE-LABELED MOLECULES COUPLED WITH PARTICLES FOR MICROARRAY-BASED ASSAYS

CROSS-REFERENCE TO RELATED APPLICATIONS

This application is the national phase of PCT application PCT/CN2010/001711 having an international filing date of Oct. 27, 2010. The content of the above-listed PCT application is incorporated herein by this reference in its entirety.

TECHNICAL FIELD

The invention is related to the area of bioassays. In particular it is related to a microarray-based method and composition for analyzing molecular interactions, e.g., multiplexed genetic analysis of nucleic acid fragments, including diagnosis of clinical samples and disease-associated testing.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 514572006600_SeqList.txt, date recorded: Oct. 26, 2015, size: 387,584 bytes)

BACKGROUND ART

In recently years, microarray technologies enable the evaluation of up to tens of thousands of molecular interactions simultaneously in a high-throughput manner. DNA microarray-based assays have been widely used, including the applications for gene expression analysis, genotyping for mutations, single nucleotide polymorphisms (SNPs), and short tandem repeats (STRs), with regard to drug discovery, disease diagnostics, and forensic purpose (Heller, Ann Rev Biomed Eng (2002) 4: 129-153; Stoughton, Ann Rev Biochem (2005) 74: 53-82; Hoheisel, Nat Rev Genet (2006) 7: 200-210). Pre-determined specific oligonucleotide probes immobilized on microarray can serve as a de-multiplexing tool to sort spatially the products from parallel reactions performed in solution (Zhu et al., Antimicrob Agents Chemother (2007) 51: 3707-3713), and even can be more general ones, i.e., the designed and optimized artificial tags or their complementary sequences employed in the universal microarray (Gerrey et al., J Mol Biol (1999) 292: 251-262; Li et al., Hum Mutat (2008) 29: 306-314). Combined with the multiplex PCR method, microarray-based assays for SNPs and gene mutations, such as deletions, insertions, and indels, thus can be carried out in routine genetic and diagnostic laboratories.

Meanwhile, protein and chemical microarrays have emerged as two important tools in the field of proteomics (Xu and Lam, J Biomed Biotechnol (2003) δ: 257-266). Specific proteins, antibodies, small molecule compounds, peptides, and carbohydrates can now be immobilized on solid surfaces to form microarrays, just like DNA microarrays. These arrays of molecules can then be probed with simple composition of molecules or complex analytes.

Interactions between the analytes and the immobilized array of molecules are evaluated with a number of different detection systems. Typically, commercial use of microarrays employs optical detection with fluorescent, chemiluminescent or enzyme labels, electrochemical detection with enzymes, ferrocene or other electroactive labels, as well as label-free detection based on surface plasmon resonance or microgravimetric techniques (Sassolas et al., Chem Rev (2008) 108: 109-139). To further simplify the assay protocol and reduce the reliance on related equipment, magnetic bead labeling was employed so that assay results could be photographed with a charge-coupled device (CCD) assisted camera or viewed under low magnification microscope (Guo et al., J Anal Sci (2007) 23: 1-4; Li et al., supra; Shlyapnikov et al., Anal Biochem (2010) 399: 125-131), and cross-reactive contacts or unspecific bonds even can be quickly eliminated by applying magnetic field or shear flow (Mulvaney et al., Anal Biochem (2009) 392: 139-144). The detection of microarray-hybridized DNA with magnetic beads thus opens a new way to routine hybridization assays which do not require precise measurements of DNA concentration in solution.

Luminophores improve the detection of target-probe binding in microarray-based assays because they exhibit variations in signal intensity or emission spectra resulting from the binding of target-probe molecular complex. Theoretically, luminophore-labeling can be integrated with magnetic beads, facilitating the process of microarray-based assays. Luminophore-labeled molecules can be coupled to magnetic beads, each of which assembles a large amount of lumiphores at the same time, yielding high intensity of luminescence. High sensitivity detection of molecular interaction thus becomes possible.

Moreover, it's still highly desirable to further improve both sensitivity and specificity of microarray-based assays, concerning with the detection of various SNPs and gene mutations, particularly in clinical settings. The main hindrance of achieving this is that, as hybridization of labeled nucleic acid targets with surface-immobilized oligonucleotide probes is the central event in the detection of nucleic acids on microarrays (Riccelli et al., Nucleic Acids Res (2001) 29: 996-1004), only one of the two strands of DNA products is available to hybridize with these probes while the other one competes with the probes for the targets, acting as a severe interfering factor. Therefore, single-stranded DNA (ssDNA) should be enriched, and considering simplicity and cost-effectiveness, asymmetric polymerase chain reaction (PCR) was recommended in our previous work after comparing several most popular methods, and a one-step asymmetric PCR without purification process was also developed successfully with its enhanced sensitivity and specificity satisfying our requirements (Gao et al., Anal Lett (2003) 33: 2849-2863; Zhu et al., supra; Li et al., supra).

For rare clinical samples and their extreme importance of accuracy in detection, the one-step asymmetric PCR-based assay is incapable to deal with, due to its low sensitivity. An alternative way we did not recommend in the previous work was to employ microspheres, preferably paramagnetic microspheres due to their easy handling and good biocompatibility, which can be further improved with the concern of sensitivity (Gao et al., supra). Through capturing double-stranded DNA fragments with microspheres and removing the unwanted strands by denaturation methods, the yielded ssDNA products were hybridized with microarrays. Theoretically, the purer and more abundance the ssDNA products can be made, the better sensitivity is expected to achieve. As the common symmetric PCR has its properties of much higher amplification efficiency and easier design of multiplexing compared with asymmetric PCR, the combination of symmetric PCR and ssDNAs prepared with this method is expected to meet the above requirement.

SUMMARY OF THE INVENTION

The present invention is directed at compositions and methods for analyzing molecular interactions, e.g., multiplex investigation of interactions between pharmaceutical compounds, and multiplex detection of genetic information using microarray-based technology combined with luminophores and particles, in particular microparticles.

In one aspect, the present invention provides a method for detecting a target molecule using a microarray, which method comprises: a) labeling the target molecule with a luminophore; b) coupling the target molecule to a particle; c) binding the target molecule that is labeled with the luminophore, and coupled to or separated from the particle, to a probe molecule immobilized on the microarray; and d) detecting the interaction between the target molecule and the probe molecule, wherein the target molecule is selected from the group consisting of a polynucleotide, a polypeptide, an antibody, a small molecule compound, a peptide and a carbohydrate.

Any suitable luminophore can be used in the present methods. A target molecule may be labeled with a fluorophore, a phosphor or a chromophore. The fluorophore may be a quantum dot, a protein (e.g., green fluorescent protein (GFP)), or a small molecule dye. The small molecule dye may be selected from the group consisting of a xanthene derivative (fluorescein, rhodamine, Oregon green, eosin, texas red, etc.), a cyanine derivative (cyanine, indocarbocyanine, oxacarbocyanine, thiacarbocyanine, merocyanine, etc.), a naphthalene derivative (dansyl and prodan derivatives), a coumarin derivative, a oxadiazole derivative (pyridyloxazole, nitrobenzoxadiazole, benzoxadiazole, etc.), a pyrene derivative (cascade blue, etc.), BODIPY, an oxazine derivative (Nile red, Nile blue, cresyl violet, oxazine 170, etc.), an acridine derivative (proflavin, acridine orange, acridine yellow, etc.), an arylmethine derivative (auramine, crystal violet, malachite green, etc.), CF dye, Alexa Fluor, Atto and Tracy, a Tetrapyrrole derivative (porphin, phtalocyanine, bilirubin, etc.), cascade yellow, azure B, acridine orange, DAPI, Hoechst 33258, lucifer yellow, piroxicam, quinine, anthraqinone, squarylium, and oligophenylene. Phosphors are transition metal compounds or rare earth compounds of various types. The chromophore may be selected from the group consisting of a retinal dye, a food coloring, a fabric dye (azo compounds), lycopene, β-carotene, anthocyanins, chlorophyll, hemoglobin, hemocyanin, a colorful mineral (malachite, amethyst, etc.).

The target molecule may be directly or indirectly labeled with a luminophore. The target molecule may be labeled with a luminophore through a modification selected from the group consisting of a chemical group, a polynucleotide, a polypeptide, an antibody, a small molecule compound, a peptide and a carbohydrate. For a double-stranded target molecule, e.g., double-stranded DNA, the strand that is coupled to the particle should be labeled with a luminophore. The target molecule may be decoupled from the particle before binding to the probe molecule immobilized on the microarray.

Any suitable particle can be used in the present methods. Each particle may be coupled with at least one target molecule. In one embodiment, the particle is a microparticle. In another embodiment, the microparticle is a paramagnetic microsphere. In some embodiments, the microparticle has a diameter from about 0.1 micrometers to about 10 micrometers.

The particle may be coated with a functional group or moiety. In one embodiment, the functional group or moiety may be selected from the group consisting of a chemical group, a polynucleotide, a polypeptide, an antibody, a small molecule compound, a peptide and a carbohydrate. In another embodiment, the chemical group may be aldehyde, hydroxyl, carboxyl, ester, amine, sulfo, or sulfhydryl. In yet another embodiment, the functional group may be selected from the group consisting of streptavidin, neutravidin and avidin. In still another embodiment, the polynucleotide is poly-dT or poly-dA.

Besides being labeled with a luminophore, the target molecule may be modified with another moiety. The moiety may be selected from the group consisting of a chemical group, a polynucleotide, a polypeptide, an antibody, a small molecule compound, a peptide and a carbohydrate. In some embodiments the chemical group may be aldehyde, hydroxyl, carboxyl, ester, amine, sulfo, or sulfhydryl. In some other embodiments, the polypeptide may be streptavidin, neutravidin, or avidin. In yet other embodiments, the polynucleotide may be poly-dT or poly-dA. In some embodiments, the target molecule is coupled to the particle through an interaction between the modification of the target molecule and the functional group or moiety on the particle. In some other embodiments, the interaction is a streptavidin-biotin interaction, a neutravidin-biotin interaction, an avidin-biotin interaction, or a poly-dT/poly-dA interaction.

The target polynucleotide may be double stranded or single stranded. In some embodiments, at least a portion of the single-stranded target polynucleotide is completely or substantially complementary to at least a portion of the oligonucleotide probe immobilized on the microarray. In other embodiments, the single-stranded target polynucleotide is completely complementary to the oligonucleotide probe immobilized on the microarray.

The target polynucleotide may be subject to an in vitro manipulation, which may produce single-stranded or double-stranded polynucleotide fragments. The target polynucleotide may be labeled with a luminophore before the in vitro manipulation, during the in vitro manipulation, or after the in vitro manipulation. In one embodiment, physical treatment is employed including laser, ultrasonication, heat, microwave, piezoelectricity, electrophoresis, dielectrophoresis, solid phase adhesion, filtration and fluidic stress. In another embodiment, the in vitro manipulation is selected from the group consisting of enzymatic digestion, PCR amplification, reverse-transcription, reverse-transcription PCR amplification, allele-specific PCR (ASPCR), single-base extension (SBE), allele specific primer extension (ASPE), restriction enzyme digestion, strand displacement amplification (SDA), transcription mediated amplification (TMA), ligase chain reaction (LCR), nucleic acid sequence based amplification (NASBA), primer extension, rolling circle amplification (RCA), self sustained sequence replication (3SR), the use of Q Beta replicase, nick translation, and loop-mediated isothermal amplification (LAMP).

For the double-stranded target polynucleotide, they may be denatured by any suitable method, e.g., a chemical reaction, an enzymatic reaction or physical treatment such as heating, or a combination thereof, before or after labeling with a luminophore and coupling with a particle. In some embodiments, the chemical reaction uses urea, formamide, methanol, ethanol, sodium hydroxide, or a combination thereof. In some embodiments, enzymatic methods include exonuclease and Uracil-N-glycosylase treatment. In other embodiments, the double-stranded target polynucleotide is heat denatured at an appropriate temperature from about 30° C. to about 95° C.

In one embodiment, the microarray comprises at least two probe molecules. In another embodiment, the microarray comprises multiple oligonucleotide probes. In yet another embodiment, the probe molecule is selected from the group consisting of a polynucleotide, a polypeptide, an antibody, a small molecule compound, a peptide and a carbohydrate.

In one embodiment, the single-stranded target polynucleotide obtained may comprise an artificially designed and optimized polynucleotide sequence such as a Tag sequence. In yet another embodiment, the microarray comprises a universal Tag array. In still another embodiment, the Tag sequences are complementary or substantially complementary to the oligonucleotide probes on the universal Tag array.

The Tm difference between different Tag sequences can be set at any suitable range, e.g., equals to or is less than about 5° C. In some embodiments, the Tag sequences have no cross-hybridization among themselves. In some other embodiments, the Tag sequences have low homology to the genomic DNA of the species. In preferred embodiments, the Tag sequences have no hair-pin structures. In one embodiment, the Tag sequence is a single stranded oligonucleotide or modified analog. In another embodiment, the Tag sequence is a locked nucleic acid (LNA), a zip nucleic acid (ZNA) or a peptide nucleic acid (PNA). In yet another embodiment, the Tag sequence is introduced to the target polynucleotide during an in vitro manipulation.

The microarray can be made by any suitable methods. In some embodiments, the microarray is fabricated using a technology selected from the group consisting of printing with fine-pointed pins, photolithography using pre-made masks, photolithography using dynamic micromirror devices, ink-jet printing, microcontact printing, and electrochemistry on microelectrode arrays. Supporting material of the microarray may be selected from the group consisting of silicon, glass, plastic, hydrogel, agarose, nitrocellulose and nylon.

The probe molecule immobilized on the microarray may be selected from the group consisting of a polynucleotide, a polypeptide, an antibody, a small molecule compound, a peptide and a carbohydrate. The probe may be attached to the microarray in any suitable fashion, such as in situ synthesis, nonspecific adsorption, specific binding, nonspecific chemical ligation, or chemoselective ligation. The binding between the probe and the microarray may be a covalent bond or physical adhesion. The supporting material of the microarray may be any suitable material, e.g., silicon, glass, plastic, hydrogel, agarose, nitrocellulose and nylon. A spot on the microarray may have any suitable size. In one embodiment, a spot on the microarray ranges from about 10 micrometers to about 5000 micrometers in diameter. In another embodiment, the oligonucleotide probe is a single stranded oligonucleotide or modified analog. In yet another embodiment, the oligonucleotide probe is a LNA, a ZNA or a PNA. The binding between the target molecule and the probe molecule may be a non-covalent, reversible covalent or irreversible covalent interaction.

An external force including a magnetic force and a dielectrophoretic force may be applied to manipulate the particle or microsphere so as to enhance the efficiency and efficacy of the binding between the target molecule and the probe molecule. The result may be detected any suitable means, e.g., with a microarray scanning device for luminescence. In one embodiment, the microarray scanning device may employ optical detection with a fluorescent label, a phosphore label, a chromophore label, or a chemiluminescent label. In another embodiment, the microarray scanning device may employ label-free detection based on surface plasmon resonance, magnetic force, giant magnetoresistance or microgravimetric technique.

In one embodiment, the target molecule is associated with a disease caused by an infectious or pathogenic agent selected from the group consisting of a fungus, a bacterium, a mycoplasma, a rickettsia, a chlamydia, a virus and a protozoa. In another embodiment, the target molecule is associated with a sexually transmitted disease, cancer, cerebrovascular disease, heart disease, respiratory disease, coronary heart disease, diabetes, hypertension, Alzheimer's disease, neurodegenerative disease, chronic obstructive pulmonary disease, autoimmune disease, cystic fibrosis, spinal muscular atrophy, beta thalassemia, phenylalanine hydroxylase deficiency, Duchenne muscular dystrophy, or hereditary hearing loss. In yet another embodiment, the target molecule is associated with hereditary hearing loss.

In another aspect, the present invention provides a method for detecting a target molecule, which method comprises: a) labeling the target molecule with a luminophore; b) coupling the target molecule to a particle; c) binding the target molecule that is labeled with the luminophore, and coupled to or separated from the particle, to a probe molecule immobilized on the microarray, d) detecting the interaction between the target molecule and the probe molecule, wherein the target molecule is associated with the genetic information, and the target molecule is selected from the group consisting of a polynucleotide, a polypeptide, an antibody, a small molecule compound, a peptide and a carbohydrate.

Any suitable genetic information can be detected by the present methods. For example, the genetic information may be a mutation selected from the group consisting of a substitution, an insertion, a deletion and an indel. In one embodiment, the genetic information is a single nucleotide polymorphism (SNP). In another embodiment, the genetic information is associated with a target molecule including a polypeptide, an antibody, a small molecule compound, a peptide and a carbohydrate.

The genetic information associated with hereditary hearing loss may be within any suitable target gene, e.g., a target gene of GJB2 (Cx26), SLC26A4 (PDS), or 12S rRNA (MTRNR1). In one embodiment, the genetic information in GJB2 is selected from the group consisting of c.35delG, c.176_191del16, c.235delC, and c.299_300delAT. In another embodiment, the genetic information in SLC26A4 is selected from the group consisting of c.2168A>G and c.919-2A>G. In yet another embodiment, the genetic information in 12S rRNA is selected from the group consisting of m.1494C>T and m.1555A>G.

The target polynucleotide containing or suspected of containing genetic information may be amplified before detection. For example, ASPCR may be used to amplify the genetic information. Any suitable or suitable set of primers can be used in amplifying the target polynucleotide containing or suspected of containing genetic information. In one embodiment, the set of primers for the ASPCR includes at least two allele-specific primers and one common primer. In another embodiment, the allele-specific primers and the common primer have a sequence as set forth in Table 2. In yet another embodiment, the allele-specific primers terminate at the SNP/mutation locus. In still another embodiment, the allele-specific primer further comprises an artificial mismatch to the wild-type sequence. In a further embodiment, the allele-specific primers comprise a natural nucleotide or analog thereof. In some embodiments, the allele-specific primers comprise a Tag sequence. In some other embodiments, the ASPCR uses a DNA polymerase without the 3' to 5' exonuclease activity.

Multiple genetic information may be detected. In one embodiment, multiplex PCR is used to amplify the genetic information. The location of an oligonucleotide probe immobilized on the microarrays may serve as a de-multiplexing tool. In some embodiments, genetic materials are isolated from tissues, cells, body fluids, hair, nail and ejaculate, including saliva sample, sputum sample, sperm sample, oocyte sample, zygote sample, lymph sample, blood sample, interstitial fluid sample, urine sample, buccal swab sample, chewing gum sample, cigarette butt sample, envelope sample, stamp sample, prenatal sample, or dried blood spot sample.

In yet another aspect, the present invention provides a composition comprising a luminophore-labeled target molecule coupled to a particle and a probe molecule immobilized on a microarray that is bound to the target molecule, wherein the target molecule is selected from the group consisting of a polynucleotide, a polypeptide, an antibody, a small molecule compound, a peptide and a carbohydrate.

In one embodiment, the oligonucleotide probe comprises a Tag sequence as set forth in Table 1. In another embodiment, the universal Tag array comprises at least two of the Tag sequences set forth in Table 1. In yet another embodiment, the universal Tag array comprises at least four of the Tag sequences set forth in Table 1. In yet another embodiment, the universal Tag array comprises at least eight of the Tag sequences set forth in Table 1. In still another embodiment, the universal Tag array comprises all of the Tag sequences set forth in Table 1.

Further provided herein is a primer comprising a sequence as set forth in Table 2 without the Tag sequence, the biotinylated universal primer sequence at the 5'-terminus, or the Cy3 label, which primer is not a full-length cDNA or a full-length genomic DNA and is selected from the group consisting of t1494C>T-WT, t1494C>T-MU, and 1494C>T-RB. In one embodiment, the primer consists essentially of the sequence as set forth in Table 2 without the Tag sequence, the biotinylated universal primer sequence at the 5'-terminus, or the Cy3 label, which primer is selected from the group consisting of t1494C>T-WT, t1494C>T-MU, and 1494C>T-RB. In another embodiment, the primer consists of the sequence as set forth in Table 2 without the Tag sequence, the biotinylated universal primer sequence at the 5'-terminus, or the Cy3 label, which primer is selected from the group consisting of t1494C>T-WT, t1494C>T-MU, and 1494C>T-RB. In some embodiments, the primer comprises the sequence as set forth in Table 2, which primer is not t35delG-WT or t35delG-MU. In some other embodiments, the primer may be labeled with a luminophore.

Also provided herein is a set of primers for ASPCR amplification of a genetic information comprising two allele-specific primers and a common primer as set forth in Table 2.

In a further aspect, the present invention provides a kit useful for detecting a genetic information comprising a universal Tag array comprising at least two of the Tag sequences as set forth in Table 1. The kit may comprise an instructional manual. In one embodiment, the kit further comprises the primer comprising a sequence as set forth in Table 2 without the Tag sequence, the biotinylated universal primer sequence at the 5'-terminus, or the Cy3 label, which primer is not a full-length cDNA or a full-length genomic DNA and is selected from the group consisting of t1494C>T-WT, t1494C>T-MU, and 1494C>T-RB. In another embodiment, the kit comprises the set of primers for ASPCR amplification of a genetic information comprising two allele-specific primers and a common primer as set forth in Table 2.

In yet a further aspect, the present invention provides a kit useful for detecting a molecular interaction comprising a luminophore, a particle and a universal Tag array comprising at least two of the Tag sequences as set forth in Table 1.

DETAILED DESCRIPTION OF THE INVENTION

Figure 1:
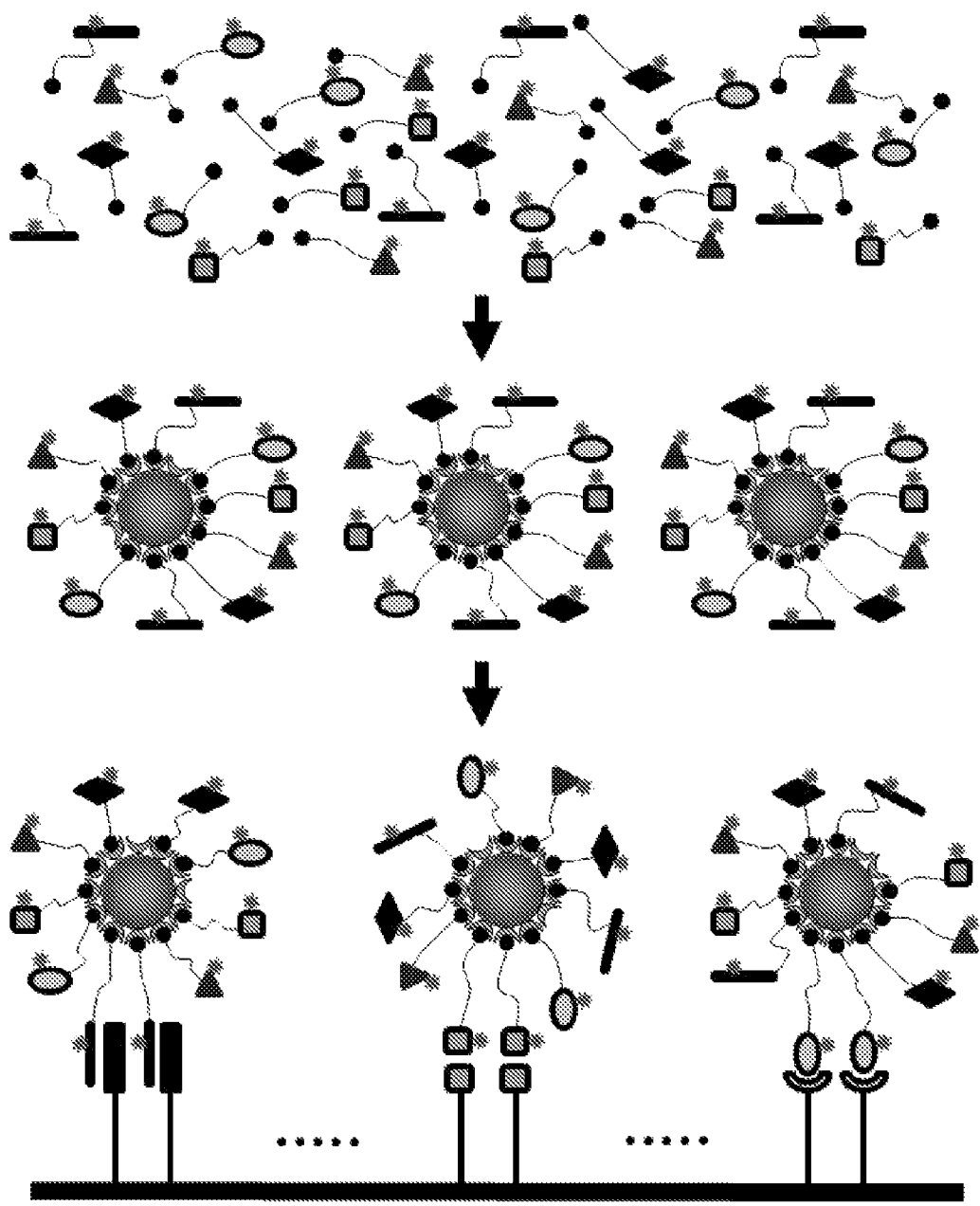
FIG. 1 is a schematic drawing in accordance with the invention of luminophore-labeled molecules coupled with particles for microarray-based assay.

The present invention provides a method that combines microarray-based assays with particles and luminophore-labeled target molecules. In some embodiments, the method combines microarray-based assays with particles, through enriching luminophore-labeled target nucleic acid fragments, then coupling particles to microarray spots through target-probe hybridization, and finally de-multiplexing. In some other embodiments, the method combines microarray-based assays with particles, through enriching luminophore-labeled double-stranded nucleic acid fragments, harvesting single-stranded nucleic acid fragments, then coupling particles to microarray spots through target-probe hybridization, and finally de-multiplexing.

Besides ensuring the high sensitivity and specificity, combining microarray-based assays with particles and luminophore-labeling facilitates the examination of assay results with appropriate devices. To prove the combinatorial method, the detection of SNP/mutation related to hereditary hearing loss was carried out as an example, demonstrating the properties of high specificity and high sensitivity of such method for multiplexed genetic analysis, especially for diagnosis of clinical samples and disease-associated genetic testing.

Before the present invention is described in detail, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

A. DEFINITIONS

As used herein, the singular forms "a", "an", and "the" include plural references unless indicated otherwise. For example, "a" dimer includes one or more dimers.

The term "molecule" is used herein to refer to any chemical or biochemical structure which includes, but is not limited to, polynucleotides, polypeptides, antibodies, small molecule compounds, peptides, and carbohydrates.

A "target" molecule refers to the molecule to be detected by the methods described in the current invention. In the case of a double stranded polynucleotide, the target molecule may refer to either or both of the complementary strands.

The term "luminophore" is used herein to refer to an atom or atomic grouping in a chemical compound that manifests luminescence.

The term "particle" or "microparticle" is meant to refer to small particles, preferred herein in diameter from about 0.01 micrometers to about 1000 micrometers. In some embodiments, a "particle" or "microparticle" includes an inherent property (e.g., magnetization, fluorescence and the like) allowing identification of each particle or microparticle as belonging to a specific group. The term "microsphere" is meant to refer to a particle, preferably spherical and usually within the range of from about 0.01 micrometers to about 1000 micrometers. In some embodiment, a microsphere may consist of one or more identifying Tags (e.g., magnetization, fluorescence and the like) formed together with a polymer, glass, or other matrix, coating or the like. The term "magnetic microsphere" is meant to refer to a particle within the range of from about 0.01 micrometers to about 1000 micrometers including one or more magnetic domains with a polymer, glass, or other matrix, coating or the like. Neither the term "microsphere" or "magnetic microsphere" is meant to exclude shapes other than spherical, and such terms are meant to include other shapes such as globular, flat and the like.

The term "microarray" is used herein to refer to polynucleotide, polypeptide or chemical microarrays. Specific polynucleotides, polypeptides, antibodies, small molecule compounds, peptides, and carbohydrates can be immobilized on solid surfaces to form microarrays.

The term "binding" is used herein to refer to an attractive interaction between two molecules which results in a stable association in which the molecules are in close proximity to each other. Molecular binding can be classified into the following types: non-covalent, reversible covalent and irreversible covalent. Molecules that can participate in molecular binding include polypeptides, polynucleotides, carbohydrates, lipids, and small organic molecules such as pharmaceutical compounds. Polypeptides that form stable complexes with other molecules are often referred to as receptors while their binding partners are called ligands. Polynucleotides can also form stable complex with themselves or others, for example, DNA-protein complex, DNA-DNA complex, DNA-RNA complex.

The term "polypeptide" is used herein to refer to proteins, fragments of proteins, and peptides, whether isolated from natural sources, produced by recombinant techniques, or chemically synthesized. A polypeptide may have one or more modifications, such as a post-translational modification (e.g., glycosylation, etc.) or any other modification (e.g., pegylation, etc.). The polypeptide may contain one or more non-naturally-occurring amino acids (e.g., such as an amino acid with a side chain modification). Polypeptides of the invention typically comprise at least about 10 amino acids.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing normucleotidic backbones, for example, polyamide (e.g., peptide nucleic acid ("PNA")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2',5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

"Nucleic acid probe" and "probe" are used interchangeably and refer to a structure comprising a polynucleotide, as defined above, that contains a nucleic acid sequence that can bind to a corresponding target. The polynucleotide regions of probes may be composed of DNA, and/or RNA, and/or synthetic nucleotide analogs.

As used herein, "complementary or matched" means that two nucleic acid sequences have at least 50% sequence identity. Preferably, the two nucleic acid sequences have at least 60%, 70%, 80%, 90%, 95%, 96%, 97%, 98%, 99% or 100% of sequence identity. "Complementary or matched" also means that two nucleic acid sequences can hybridize under low, middle and/or high stringency condition(s). The percentage of sequence identity or homology is calculated by comparing one to another when aligned to corresponding portions of the reference sequence.

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s). The percentage of sequence identity or homology is calculated by comparing one to another when aligned to corresponding portions of the reference sequence.

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions are conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization refers to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See M. Kanehisa Nucleic Acids Res. 12:203 (1984).

The terms "homologous", "substantially homologous", and "substantial homology" as used herein denote a sequence of amino acids having at least 50%, 60%, 70%, 80% or 90% identity wherein one sequence is compared to a reference sequence of amino acids. The percentage of sequence identity or homology is calculated by comparing one to another when aligned to corresponding portions of the reference sequence.

"Multiplexing" or "multiplex assay" herein refers to an assay or other analytical method in which the presence of multiple target molecules can be assayed simultaneously by using more than one capture probe conjugate, each of which has at least one different detection characteristic, e.g., fluorescence characteristic (for example excitation wavelength, emission wavelength, emission intensity, FWHM (full width at half maximum peak height), or fluorescence lifetime).

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

B. LUMINOPHORE

A luminophore is an atom or atomic grouping in a chemical compound that manifests luminescence. There exist organic and inorganic luminophores. Luminophores can be divided into two subcategories: fluorophores and phosphors. The difference between luminophores belonging to these two subcategories is derived from the nature of the excited state responsible for the emission of photons. Some luminophores, however, cannot be classified as being exclusively fluorophores or phosphors and exist in the gray area in between. Such cases include transition metal complexes (such as ruthenium tris-2,2'-bipyridine) whose luminescence comes from an excited (nominally triplet) metal-to-ligand charge transfer (MLCT) state, but which is not a true triplet-state in the strict sense of the definition. Most luminophores consist of conjugated pi systems or transition metal complexes. There exist purely inorganic luminophores, such as zinc sulfide doped with rare earth metal ions, rare earth metal oxysulfides doped with other rare earth metal ions, yttrium oxide doped with rare earth metal ions, zinc orthosilicate doped with manganese ions, etc.

A chromophore is a region in a molecule where the energy difference between two different molecular orbitals falls within the range of the visible spectrum. Visible light that hits the chromophore can thus be absorbed by exciting an electron from its ground state into an excited state. In biological molecules that serve to capture or detect light energy, the chromophore is the moiety that causes a conformational change of the molecule when hit by light. Chromophores almost always arise in one of two forms: conjugated pi systems and metal complexes. In the former, the energy levels that the electrons jump between are extended pi orbitals created by a series of alternating single and double bonds, often in aromatic systems. Common examples include retinal (used in the eye to detect light), various food colorings, fabric dyes (azo compounds), lycopene, β-carotene, and anthocyanins. The metal complex chromophores arise from the splitting of d-orbitals by binding of a transition metal to ligands. Examples of such chromophores can be seen in chlorophyll (used by plants for photosynthesis), hemoglobin, hemocyanin, and colorful minerals such as malachite and amethyst.

A fluorophore, in analogy to a chromophore, is a component of a molecule which causes a molecule to be fluorescent. It is a functional group in a molecule which will absorb energy of a specific wavelength and re-emit energy at a different (but equally specific) wavelength. The amount and wavelength of the emitted energy depend on both the fluorophore and the chemical environment of the fluorophore. This technology has particular importance in the field of biochemistry and protein studies, e.g., in immunofluorescence and immunohistochemistry. Fluorescein isothiocyanate (FITC), a reactive derivative of fluorescein, has been one of the most common fluorophores chemically attached to other, non-fluorescent molecules to create new fluorescent molecules for a variety of applications. Other common fluorophores include derivatives of rhodamine (TRITC), coumarin, cyanine, the CF Dyes, the FluoProbes, the DyLight Fluors, the Oyester (dyes), the Atto dyes, the HiLyte Fluors, and the Alexa Fluors.

These fluorophores can be quantum dots, protein (e.g., green fluorescent protein (GFP)) or small molecules. Common small molecule dye families include: xanthene derivatives (fluorescein, rhodamine, Oregon green, eosin, texas red, etc.), cyanine derivatives (cyanine, indocarbocyanine, oxacarbocyanine, thiacarbocyanine, merocyanine, etc.), naphthalene derivatives (dansyl and prodan derivatives), coumarin derivatives, oxadiazole derivatives (pyridyloxazole, nitrobenzoxadiazole, benzoxadiazole, etc.), pyrene derivatives (cascade blue, etc.), BODIPY (Invitrogen), oxazine derivatives (Nile red, Nile blue, cresyl violet, oxazine 170, etc.), acridine derivatives (proflavin, acridine orange, acridine yellow, etc.), arylmethine derivatives (auramine, crystal violet, malachite green, etc.), CF dye (Biotium), Alexa Fluor (Invitrogen), Atto and Tracy (Sigma), Tetrapyrrole derivatives (porphin, phtalocyanine, bilirubin, etc.), and others (cascade yellow, azure B, acridine orange, DAPI, Hoechst 33258, lucifer yellow, piroxicam, quinine and anthraqinone, squarylium, oligophenylenes, etc.).

Phosphors are transition metal compounds or rare earth compounds of various types. A material can emit light either through incandescence, where all atoms radiate, or by luminescence, where only a small fraction of atoms, called emission centers or luminescence centers, emit light. In inorganic phosphors, these inhomogeneities in the crystal structure are created usually by addition of a trace amount of dopants, impurities called activators. (In rare cases dislocations or other crystal defects can play the role of the impurity.) The wavelength emitted by the emission center is dependent on the atom itself, and on the surrounding crystal structure.

The scintillation process in inorganic materials is due to the electronic band structure found in the crystals. An incoming particle can excite an electron from the valence band to either the conduction band or the exciton band (located just below the conduction band and separated from the valence band by an energy gap). This leaves an associated hole behind, in the valence band. Impurities create electronic levels in the forbidden gap. The excitons are loosely bound electron-hole pairs which wander through the crystal lattice until they are captured as a whole by impurity centers. The latter then rapidly de-excite by emitting scintillation light (fast component). In case of inorganic scintillators, the activator impurities are typically chosen so that the emitted light is in the visible range or near-UV where photomultipliers are effective. The holes associated with electrons in the conduction band are independent from the latter. Those holes and electrons are captured successively by impurity centers exciting certain metastable states not accessible to the excitons. The delayed de-excitation of those metastable impurity states, slowed down by reliance on the low-probability forbidden mechanism, again results in light emission (slow component).

C. MICROARRAY

In a high-throughput manner, microarray technologies enable the evaluation of up to tens of thousands of molecular interactions simultaneously. Microarrays have made significant impact on biology, medicine, drug discovery. DNA microarray-based assays have been widely used, including the applications for gene expression analysis, genotyping for mutations, single nucleotide polymorphisms (SNPs), and short tandem repeats (STRs). And polypeptide and chemical microarrays have emerged as two important tools in the field of proteomics. Chemical microarray, a form of combinatorial libraries, can also be used for lead identification, as well as optimization of these leads. In this era of bioterrorism, the development of a microarray capable of detecting a multitude of biological or chemical agents in the environment will be of great interest to the law enforcement agencies.

According to some embodiments of the present invention, assay methods for analysis of molecular interactions are provided. According to some embodiments of the present invention, assay methods for multiplexed analysis of target polynucleotides are provided. The inventive technology improves specificity and sensitivity of microarray-based assays while reducing the cost of performing genetic assays.

FIG. 1 shows, with a schematic drawing, the invention of luminophore-labeled target molecules coupled with particles for microarray-based assay. The target molecules include polynucleotides, polypeptides, antibodies, small molecule compounds, peptides, and carbohydrates.

As those of ordinary skill in the art will recognize, this invention has an enormous number of applications, especially in assays and techniques for pharmaceutical development and diagnostics. The assays may be designed, for example, to detect polynucleotide molecules associated with any of a number of infectious or pathogenic agents including fungi, bacteria, mycoplasma, rickettsia, chlamydia, viruses, and protozoa, or to detect polynucleotide fragments associated with sexually transmitted disease, pulmonary disorders, gastrointestinal disorders, cardiovascular disorders, etc.

A microarray is a multiplex technology widely used in molecular biology and medicine. Microarrays can be fabricated using a variety of technologies, including printing with fine-pointed pins, photolithography using pre-made masks, photolithography using dynamic micromirror devices, ink-jet printing, microcontact printing, or electrochemistry on microelectrode arrays. In standard microarrays, the probe molecules are attached via surface engineering to a solid surface of supporting materials, which include glass, silicon, plastic, hydrogels, agaroses, nitrocellulose and nylon.

Figure 2:
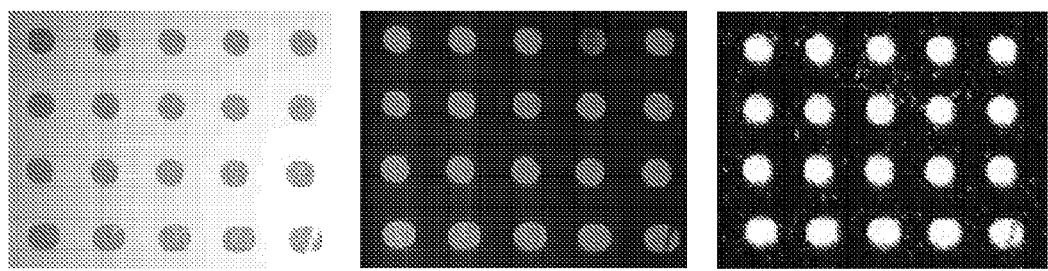
FIG. 2 shows, for the detection of fluorescence-labeled target molecules, an experimental result viewed with three different methods, i.e., by a CCD in bright field (left panel), under a fluorescence microscopy (middle panel), and by a commercial fluorescence microarray scanner with pseudo-color processing (right panel).

As FIG. 2 shows, the microarray results for the detection of fluorescence-labeled target molecules can be viewed with three different methods, i.e., by a CCD in bright field (left panel), under a fluorescence microscopy (middle panel), and by a commercial fluorescence microarray scanner with pseudo-color processing (right panel).

For DNA microarray, it comprises or consists of an arrayed series of microscopic spots of DNA oligonucleotides, known as probes. This can be a short section of a gene or other DNA element that are used to hybridize a complementary polynucleotide sample (called target) under stringent conditions. Targets in solution are usually detected and quantified by detection of fluorophore-, silver-, or chemiluminescence-labeled targets hybridized on microarray. Since an array can contain several to tens of thousands of probes, a microarray experiment can accomplish many genetic tests in parallel.

The systems described herein may comprise two or more probes that detect the same target polynucleotide. For example, in some embodiments where the system is a microarray, the probes may be present in multiple (such as any of 2, 3, 4, 5, 6, 7, or more) copies on the microarray. In some embodiments, the system comprises different probes that detect the same target polynucleotide. For example, these probes may bind to different (overlapping or nonoverlapping) regions of the target polynucleotide.

Any probes that are capable of determining the levels of target polynucleotide can be used. In some embodiments, the probe may be an oligonucleotide. It is understood that, for detection of target polynucleotides, certain sequence variations are acceptable. Thus, the sequence of the oligonucleotides (or their complementary sequences) may be slightly different from those of the target polynucleotides described herein. Such sequence variations are understood by those of ordinary skill in the art to be variations in the sequence that do not significantly affect the ability of the oligonucleotide to determine target polynucleotide levels. For example, homologs and variants of these oligonucleotide molecules possess a relatively high degree of sequence identity when aligned using standard methods. Oligonucleotide sequences encompassed by the present invention have at least 40%, including for example at least about any of 50%, 60%, 70%, 80%, 90%, 95%, or more sequence identity to the sequence of the target polynucleotides described herein. In some embodiments, the oligonucleotide comprises a portion for detecting the target polynucleotides and another portion. Such other portion may be used, for example, for attaching the oligonucleotides to a substrate. In some embodiments, the other portion comprises a non-specific sequence (such as poly-T or poly-dT) for increasing the distance between the complementary sequence portion and the surface of the substrate.

The oligonucleotides for the systems described herein include, for example, DNA, RNA, PNA, ZNA, LNA, combinations thereof, and/or modified forms thereof. They may also include a modified oligonucleotide backbone. In some embodiments, the oligonucleotide comprises at least about any of 5, 6, 7, 8, 9, 10, 12, 13, 14, 15, 16, 17, 18, 19, 20, or more continuous oligonucleotides complementary or identical to all or part of target polynucleotides described herein. A single oligonucleotide may comprise two or more such complementary sequences. In some embodiments, there may be a reactive group (such as an amine) attached to the 5' or 3' end of the oligonucleotide for attaching the oligonuceotide to a substrate.

In some embodiments, the probes are oligonucleotides. Oligonucleotides forming the array may be attached to the substrate by any number of ways including, but not limiting to, (i) in situ synthesis (e.g., high-density oligonucleotide arrays) using photolithographic techniques; (ii) spotting/printing at medium to low density on glass, silicon, nylon or nitrocellulose; (iii) masking; and (iv) dot-blotting on a nylon or nitrocellulose hybridization membrane. Oligonucleotides may also be non-covalently immobilized on the substrate by binding to anchors in a fluid phase such as in microtiter wells, microchannels or capillaries.

Several techniques are well-known in the art for attaching polynucleotides to a solid substrate such as a glass slide. One method is to incorporate modified bases or analogs that contain a moiety that is capable of attachment to a solid substrate, such as an amine group, a derivative of an amine group or another group with a positive charge, into the amplified polynucleotides. The amplified product is then contacted with a solid substrate, such as a glass slide, which may be coated with an aldehyde or another reactive group which can form a covalent link with the reactive group that is on the amplified product and become covalently attached to the glass slide. Microarrays comprising the amplified products can be fabricated using a Biodot (BioDot, Inc. Irvine, Calif.) spotting apparatus and aldehyde-coated glass slides (CEL Associates, Houston, Tex.). Amplification products can be spotted onto the aldehyde-coated slides, and processed according to published procedures (Schena et al., Proc. Natl. Acad. Sci. U.S.A. (1995), 93:10614-10619). Arrays can also be printed by robotics onto glass, nylon (Ramsay, G., Nature Biotechnol. (1998), 16:40-44), polypropylene (Matson, et al., Anal Biochem. (1995), 224(1):110-6), and silicone slides (Marshall and Hodgson, Nature Biotechnol. (1998), 16:27-31). Other approaches to array assembly include fine micropipetting within electric fields (Marshall, and Hodgson, Nature Biotechnol. (1998), 16:27-31), and spotting the polynucleotides directly onto positively coated plates. Methods such as those using amino propyl silicon surface chemistry are also known in the art, as disclosed at http://cmgm.stanford.edu/pbrown/.

The assays of the present invention may be implemented in a multiplex format. Multiplex methods are provided employing 2, 3, 4, 5, 10, 15, 20, 25, 50, 100, 200, 500, 1000 or more different capture probes which can be used simultaneously to assay for amplification products from corresponding different target polynucleotides. In some embodiments, multiplex methods can also be used to assay for polynucleotide target sequences which have not undergone an amplification procedure. Methods amenable to multiplexing, such as those taught herein, allow acquisition of greater amounts of information from smaller specimens. The need for smaller specimens increases the ability of an investigator to obtain samples from a larger number of individuals in a population to validate a new assay or simply to acquire data, as less invasive techniques are needed.

Where different substrates are included in a multiplex assay as part of the capture probe conjugates, the different substrates can be encoded so that they can be distinguished. Any encoding scheme can be used; conveniently, the encoding scheme can employ one or more different fluorophores, which can be fluorescent semiconductor nanocrystals. High density spectral coding schemes can be used.

One or more different populations of spectrally encoded capture probe conjugates can be created, each population comprising one or more different capture probes attached to a substrate comprising a known or determinable spectral code comprising one or more semiconductor nanocrystals or fluorescent nanoparticle. Different populations of the conjugates, and thus different assays, can be blended together, and the assay can be performed in the presence of the blended populations. The individual conjugates are scanned for their spectral properties, which allows the spectral code to be decoded and thus identifies the substrate, and therefore the capture probe(s) to which it is attached. Because of the large number of different semiconductor nanocrystals and fluorescent nanoparticles and combinations thereof which can be distinguished, large numbers of different capture probes and amplification products can be simultaneously interrogated.

D. PARTICLES

The present invention provides particles, microparticles or beads, preferably magnetic beads, to be used for the microarray-based assay. Particles or beads can be prepared from a variety of different polymers, including but not limited to polystyrene, cross-linked polystyrene, polyacrylic acid, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers and epoxies. The materials have a variety of different properties with regard to swelling and porosity, which are well understood in the art. Preferably, the beads are in the size range of approximately 10 nanometers to 1 millimeter, preferably 100 nanometers to 10 micrometers, and can be manipulated using normal solution techniques when suspended in a solution. The terms "particle," "bead," "sphere," "microparticle," "microbead" and "microsphere" are used interchangeably herein.

The suitable chemical compositions for the magnetic particles may be ferromagnetic materials and include rare earth containing materials such as, e.g., iron-cobalt, iron-platinum, samarium-cobalt, neodynium-iron-boride, and the like. Other magnetic materials, e.g., superparamagnetic materials such as iron oxides ($Fe_3O_4$) may be used as well. Among the preferred magnetic materials are included iron-cobalt as such material is generally easier to magnetize, has a stronger magnetization (about 1.7 Tesla) and is less susceptible to corrosion.

Because of the use of particles, expensive readout devices for results may not be necessary. Particles on the microarray spots can be viewed directly with naked eyes if the sizes in diameters of these spots are larger than 0.03 millimeters. In another way, assay results with any spot sizes, from 0.01 millimeters to 5 millimeters in diameter, can be photographed with an ordinary camera or viewed under an appropriate magnification microscope.

E. TARGET POLYNUCLEOTIDE

The target polynucleotide can be single-stranded, double-stranded, or higher order, and can be linear or circular. Exemplary single-stranded target polynucleotides include mRNA, rRNA, tRNA, hnRNA, microRNA, ssRNA or ssDNA viral genomes and viroids, although these polynucleotides may contain internally complementary sequences and significant secondary structure. Exemplary double-stranded target polynucleotides include genomic DNA, mitochondrial DNA, chloroplast DNA, dsRNA or dsDNA viral genomes, plasmids, phages, shRNA (a small hairpin RNA or short hairpin RNA), and siRNA (small/short interfering RNA). The target polynucleotide can be prepared recombinantly, synthetically or purified from a biological source. The target polynucleotide may be purified to remove or diminish one or more undesired components of the sample or to concentrate the target polynucleotide prior to amplification. Conversely, where the target polynucleotide is too concentrated for a particular assay, the target polynucleotide may first be diluted.

Following sample collection and optional nucleic acid extraction and purification, the nucleic acid portion of the sample comprising the target polynucleotide can be subjected to one or more preparative treatments. These preparative treatments can include in vitro transcription (IVT), labeling, fragmentation, amplification and other reactions. mRNA can first be treated with reverse transcriptase and a primer, which can be the first primer comprising the target noncomplementary region, to create cDNA prior to detection and/or further amplification; this can be done in vitro with extracted or purified mRNA or in situ, e.g., in cells or tissues affixed to a slide. Nucleic acid amplification increases the copy number of sequences of interest and can be used to incorporate a label into an amplification product produced from the target polynucleotide using a labeled primer or labeled nucleotide. A variety of amplification methods are suitable for use, including the polymerase chain reaction method (PCR), transcription mediated amplification (TMA), the ligase chain reaction (LCR), self sustained sequence replication (3SR), nucleic acid sequence-based amplification (NASBA), rolling circle amplification (RCA), loop-mediated isothermal amplification (LAMP), the use of Q Beta replicase, reverse transcription, nick translation, and the like, particularly where a labeled amplification product can be produced and utilized in the methods taught herein.

Any nucleotides may be detected by the present devices and methods. Examples of such nucleotides include AMP, GMP, CMP, UMP, ADP, GDP, CDP, UDP, ATP, GTP, CTP, UTP, dAMP, dGMP, dCMP, dTMP, dADP, dGDP, dCDP, dTDP, dATP, dGTP, dCTP and dTTP.

In some embodiments, the target polynucleotide does not have a label directly incorporated in the sequence. When the target polynucleotide is made with a directly incorporated label or so that a label can be directly bound to the target polynucleotide, this label is one which does not interfere with detection of the capture probe conjugate substrate and/or the report moiety label.

Where the target polynucleotide is single-stranded, the first cycle of amplification forms a primer extension product complementary to the target polynucleotide. If the target polynucleotide is single-stranded RNA, a reverse transcriptase is used in the first amplification to reverse transcribe the RNA to DNA, and additional amplification cycles can be performed to copy the primer extension products. The primers for a PCR must, of course, be designed to hybridize to regions in their corresponding template that will produce an amplifiable segment; thus, each primer must hybridize so that its 3' nucleotide is base-paired with a nucleotide in its corresponding template strand that is located 3' from the 3' nucleotide of the primer used to prime the synthesis of the complementary template strand.

The target polynucleotide may be amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity which can copy the target polynucleotide can be used, including DNA polymerases, RNA polymerases, reverse transcriptases, enzymes having more than one type of polymerase activity. The polymerase can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase™ T7, Sequenase™ Version 2.0 T7, Tub, Taq, Tth, Pfx, Pfu, Tsp, Tfl, Tli and *Pyrococcus* sp GB-D DNA polymerases; RNA polymerases such as *E. coli*, SP6, T3 and T7 RNA polymerases; and reverse transcriptases such as AMV, M-MuLV, MMLV, RNAse H minus MMLV (SuperScript™), SuperScript™ II, ThermoScript™, HIV-1, and RAV2 reverse transcriptases. All of these enzymes are commercially available. Exemplary polymerases with multiple specificities include RAV2 and Tli (exo-) polymerases. Exemplary thermostable polymerases include Tub, Taq, Tth, Pfx, Pfu, Tsp, Tfl, Tli and *Pyrococcus* sp. GB-D DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions, optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different regions of a particular polynucleotide within the sample. Where the amplification reaction comprises multiple cycles of amplification with a polymerase, as in PCR, it is desirable to dissociate the primer extension product(s) formed in a given cycle from their template(s). The reaction conditions are therefore altered between cycles to favor such dissociation; typically this is done by elevating the temperature of the reaction mixture, but other reaction conditions can be altered to favor dissociation, for example lowering the salt concentration and/or raising the pH of the solution in which the double-stranded polynucleotide is dissolved. Although it is preferable to perform the dissociation in the amplification reaction mixture, the polynucleotides may be first isolated using any effective technique and transferred to a different solution for dissociation, then reintroduced into an amplification reaction mixture for additional amplification cycles.

This assay can be multiplexed, i.e., multiple distinct assays can be run simultaneously, by using different pairs of primers directed at different targets, which can be unrelated targets, or different alleles or subgroups of alleles from, or chromosomal rearrangements at, the same locus. This allows the quantitation of the presence of multiple target polynucleotides in a sample (e.g., specific genes in a cDNA library). All that is required is an ability to uniquely identify the different second polynucleotide extension products in such an assay, through either a unique capture sequence or a unique label.

Amplified target polynucleotides may be subjected to post-amplification treatments. For example, in some cases, it may be desirable to fragment the amplification products prior to hybridization with a polynucleotide array, in order to provide segments which are more readily accessible and which avoid looping and/or hybridization to multiple capture probes. Fragmentation of the polynucleotides can be carried out by any method producing fragments of a size useful in the assay being performed; suitable physical, chemical and enzymatic methods are known in the art.

Figure 3:
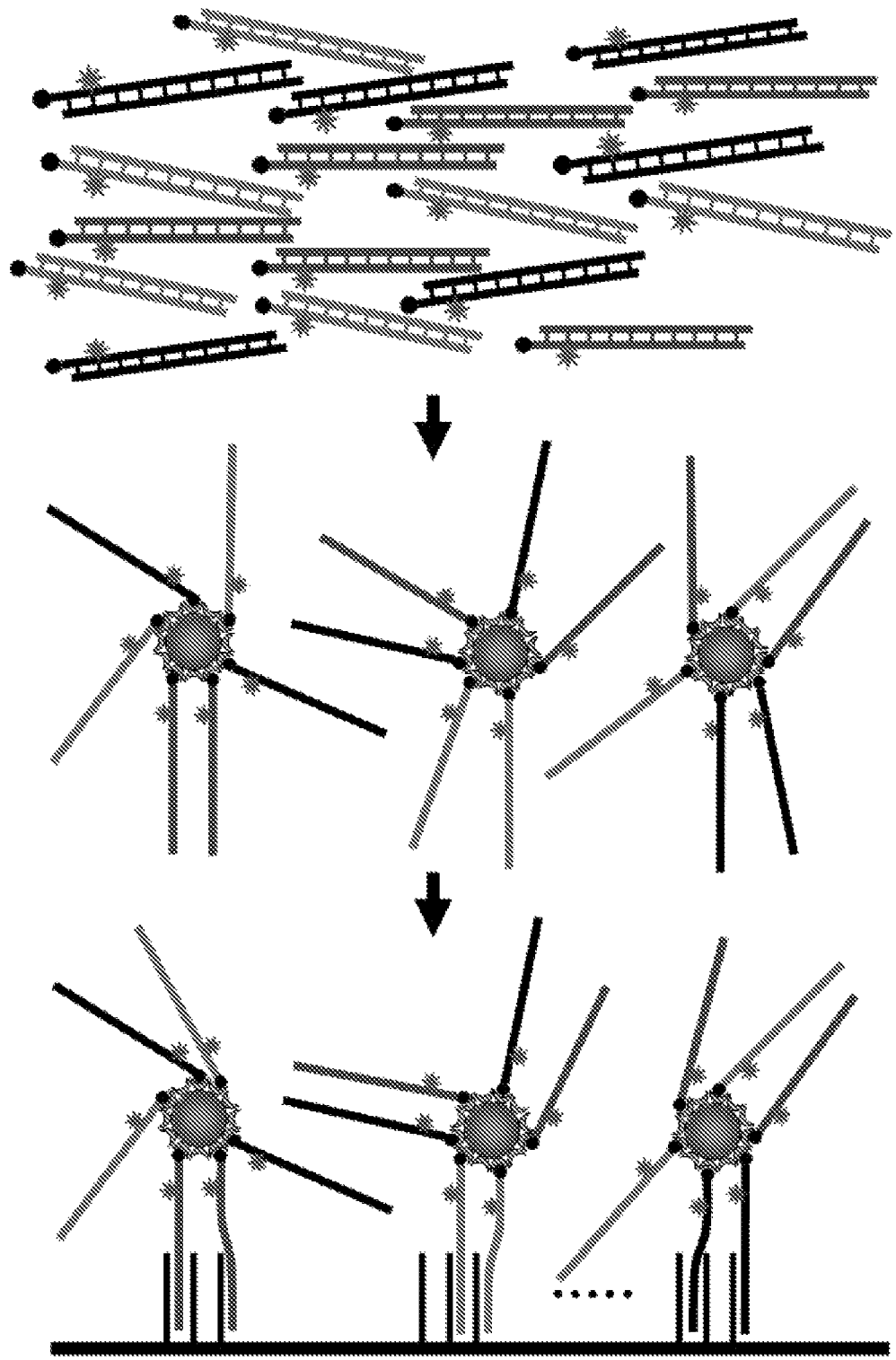
FIG. 3 is a schematic drawing in accordance with the invention of microarray-based assay integrated with particles for detection of luminophore-labeled double-stranded target polynucleotides.

Amplified target polynucleotides may also be coupled to the particles, either directly or through modifications to the polynucleotides and/or the particles (FIG. 3). In some embodiments, the target polynecleotides are modified, such as biotinylation. In some other embodiments, the particles are modified with a functional group, such as streptavidin, neutravidin, avidin, etc. The target polynucleotides may be coupled to the particles through such modifications and functional groups. For double stranded polynucleotides, following the coupling of the target polynucleotides to the particles, single-stranded target polynucleotides can be prepared by denaturation methods by a chemical reaction, enzyme or heating, or a combination thereof, while coupled to the particles. In some embodiments, the chemical reaction uses urea, formamide, methanol, ethanol, an enzyme, or NaOH. In some embodiments, enzymatic methods include exonuclease and Uracil-N-glycosylase. In some other embodiments, the double-stranded target polynucleotide is heat denatured at an appropriate temperature from about 30° C. to about 95° C.

The method of the present invention is suitable for use in a homogeneous multiplex analysis of multiple target polynucleotides in a sample. Multiple target polynucleotides can be generated by amplification of a sample by multiple amplification oligonucleotide primers or sets of primers, each primer or set of primers specific for amplifying a particular polynucleotide target sequence. For example, a sample can be analyzed for the presence of multiple viral polynucleotide target sequences by amplification with primers specific for amplification of each of multiple viral target sequences, including, e.g., human immunodeficiency virus (HIV), hepatitis B virus (HBV), hepatitis C virus (HCV), hepatitis A virus (HAV), parvovirus B19, West Nile Virus, hantavirus, severe acute respiratory syndrome-associated coronavirus (SARS), etc.

The portion of the sample comprising or suspected of comprising the target polynucleotide can be any source of biological material which comprises polynucleotides that can be obtained from a living organism directly or indirectly, including cells, tissue or fluid, and the deposits left by that organism, including viruses, mycoplasma, and fossils. The sample can also comprise a target polynucleotide prepared through synthetic means, in whole or in part. Typically, the sample is obtained as or dispersed in a predominantly aqueous medium. Nonlimiting examples of the sample include blood, plasma, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, samples of in vitro cell culture constituents (including but not limited to conditioned medium resulting from the growth of cells in cell culture medium, putatively virally infected cells, recombinant cells, and cell components), and a recombinant source, e.g., a library, comprising polynucleotide sequences.

The sample can be a positive control sample which is known to contain the target polynucleotide or a surrogate thereof. A negative control sample can also be used which, although not expected to contain the target polynucleotide, is suspected of containing it, and is tested in order to confirm the lack of contamination by the target polynucleotide of the reagents used in a given assay, as well as to determine whether a given set of assay conditions produces false positives (a positive signal even in the absence of target polynucleotide in the sample).

The sample can be diluted, dissolved, suspended, extracted or otherwise treated to solubilize and/or purify any target polynucleotide present or to render it accessible to reagents which are used in an amplification scheme or to detection reagents. Where the sample contains cells, the cells can be lysed or permeabilized to release the polynucleotides within the cells. Permeabilization buffers can be used to lyse cells which allow further steps to be performed directly after lysis, for example a polymerase chain reaction.

F. GENETIC INFORMATION

Any kind of genetic information can be the subject of the presently claimed method of microarray based analysis. For example, the genetic information may be a mutation selected from the group consisting of a substitution, an insertion, a deletion and an indel. In one embodiment, the genetic information is a single nucleotide polymorphism (SNP). In one embodiment, the genetic information is a gene. In one embodiment, the genetic information is a genetic product including a polypeptide, an antibody, a small molecule compound, a peptide and a carbohydrate. In another embodiment, the genetic information is associated with a disease caused by an infectious or pathogenic agent selected from the group consisting of a fungus, a bacterium, a mycoplasma, a rickettsia, a chlamydia, a virus and a protozoa. In yet another embodiment, the genetic information is associated with a sexually transmitted disease, cancer, cerebrovascular disease, heart disease, respiratory disease, coronary heart disease, diabetes, hypertension, Alzheimer's disease, neurodegenerative disease, chronic obstructive pulmonary disease, autoimmune disease, cystic fibrosis, spinal muscular atrophy, beta thalassemia, phenylalanine hydroxylase deficiency, Duchenne muscular dystrophy, or hereditary hearing loss. In still another embodiment, the genetic information is associated with hereditary hearing loss.

The allele of the target gene may be caused by single base substitution, insertion, or deletion, or by multiple-base substitution, insertion or deletion, or indel. Furthermore, modifications to nucleotidic units include rearranging, appending, substituting for or otherwise altering functional groups on the purine or pyrimidine base which form hydrogen bonds to a respective complementary pyrimidine or purine. The resultant modified nucleotidic unit optionally may form a base pair with other such modified nucleotidic units but not with A, T, C, G or U. Basic sites may be incorporated which do not prevent the function of the polynucleotide. Some or all of the residues in the polynucleotide can optionally be modified in one or more ways.

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-O-D-ribofuran-osyl-purine) may be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine) results in a modified nucleotide which will not effectively base pair with guanosine but will form a base pair with isoguanosine (U.S. Pat. No. 5,681,702). Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al. (1993) J. Am. Chem. Soc. 115:4461-4467 and references cited therein; and isoguanine nucleotides may be prepared using the method described by Switzer et al. (1993), supra, and Mantsch et al. (1993) Biochem. 14:5593-5601, or by the method described in U.S. Pat. No. 5,780,610. Other normatural base pairs may be synthesized by the method described in Piccirilli et al. (1990) Nature 343:33-37 for the synthesis of 2,6-diaminopyrimidine and its complement (1-methylpyrazolo-[4,3]pyrimidine-5,7-(4H,6H)-dione). Other such modified nucleotidic units which form unique base pairs are known, such as those described in Leach et al. (1992) J. Am. Chem. Soc. 114:3675-3683 and Switzer et al., supra.

A polymorphic region as defined herein is a portion of a genetic locus that is characterized by at least one polymorphic site. A genetic locus is a location on a chromosome which is associated with a gene, a physical feature, or a phenotypic trait. A polymorphic site is a position within a genetic locus at which at least two alternative sequences have been observed in a population. A polymorphic region as defined herein is said to "correspond to" a polymorphic site, that is, the region may be adjacent to the polymorphic site on the 5' side of the site or on the 3' side of the site, or alternatively may contain the polymorphic site. A polymorphic region includes both the sense and antisense strands of the polynucleotide comprising the polymorphic site, and may have a length of from about 100 to about 5000 base pairs. For example, a polymorphic region may be all or a portion of a regulatory region such as a promoter, 5' UTR, 3' UTR, an intron, an exon, or the like. A polymorphic or allelic variant is a genomic DNA, cDNA, mRNA or polypeptide having a nucleotide or amino acid sequence that comprises a polymorphism. A polymorphism is a sequence variation observed at a polymorphic site, including nucleotide substitutions (single nucleotide polymorphisms or SNPs), insertions, deletions, indels and microsatellites. Polymorphisms may or may not result in detectable differences in gene expression, protein structure, or protein function. Preferably, a polymorphic region of the present invention has a length of about 1000 base pairs. More preferably, a polymorphic region of the invention has a length of about 500 base pairs. Most preferably, a polymorphic region of the invention has a length of about 200 base pairs.

A haplotype as defined herein is a representation of the combination of polymorphic variants in a defined region within a genetic locus on one of the chromosomes in a chromosome pair. A genotype as used herein is a representation of the polymorphic variants present at a polymorphic site.

Those of ordinary skill will recognize that oligonucleotides complementary to the polymorphic regions described herein must be capable of hybridizing to the polymorphic regions under conditions of stringency such as those employed in primer extension-based sequence determination methods, restriction site analysis, nucleic acid amplification methods, ligase-based sequencing methods, mismatch-based sequence determination methods, microarray-based sequence determination methods, and the like.

Congenital hearing loss affects one in 1,000 live births and approximately 50% of these cases are hereditary. Among Chinese disabled persons, hearing loss population is the second largest. SNPs/mutations in GJB2, SLC26A4 and 12S rRNA are the prevalent causes of inherited hearing loss. This invention can meet the need of SNP/mutation detection from various deafness patients or even healthy persons, which also serves as an example to support the applicability of this innovative technology.

G. OLIGONUCLEOTIDE PRIMERS FOR AMPLIFICATION OF TARGET POLYNUCLEOTIDES

In certain aspect, the invention is also embodied in oligonucleotide primer pairs suitable for use in the polymerase chain reaction (PCR) or in other nucleic acid amplification methods. Those of ordinary skill will be able to design suitable oligonucleotide primer pairs using knowledge readily available in the art, in combination with the teachings herein. Specific oligonucleotide primer pairs of this embodiment include the oligonucleotide primer pairs set forth in Table 2, which are suitable for amplifying the polymorphic regions corresponding to polymorphic sites in GJB2, SLC26A4 and 12S rRNA. Those of ordinary skill will recognize that other oligonucleotide primer pairs suitable for amplifying the polymorphic regions in GJB2, SLC26A4 and 12S rRNA can be designed without undue experimentation.

In some variations a SNP/mutation corresponds to at least two allele-specific primers. One allele-specific primer comprises a sequence identical or complementary to a region of the wild-type allele of a target fragment containing the SNP/mutation locus. Each of the other allele-specific primers comprises a sequence identical or complementary to a region of the mutant allele of a target fragment containing the SNP/mutation locus. The allele-specific primers may terminate at their 3' ends at the SNP/mutation locus. To increase the capability of differentiation between the wild-type and mutant alleles of target genes, an artificial mismatch in the allele-specific primers may be introduced. The artificial mismatch can be a natural base or a nucleotide analog. Each of the PCR primer pairs of the invention may be used in any PCR method. For example, a PCR primer pair of the invention may be used in the methods disclosed in U.S. Pat. Nos. 4,683,195; 4,683, 202; 4,965,188; 5,656,493; 5,998,143; 6,140,054; WO 01/27327; WO 01/27329; and the like. The PCR primer pairs of the invention may also be used in any of the commercially available machines that perform PCR, such as any of the GeneAmp® Systems available from Applied Biosystems.

The present primers can comprise any suitable types of nucleic acids, e.g., DNA, RNA, PNA or a derivative thereof. Preferably, the primers comprise a nucleotide sequence, or a complementary strand thereof, that is set forth in Table 2. Also preferably, the primers are labeled, e.g., a chemical, an enzymatic, an immunogenic, a radioactive, a fluorescent, a luminescent and a FRET label.

The oligonucleotide primers can be produced by any suitable method. For example, the primers can be chemically synthesized (See generally, Ausubel (Ed.) Current Protocols in Molecular Biology, 2.11. Synthesis and purification of oligonucleotides, John Wiley & Sons, Inc. (2000)), isolated from a natural source, produced by recombinant methods or a combination thereof. Synthetic oligonucleotides can also be prepared by using the triester method of Matteucci et al., J. Am. Chem. Soc., 3:3185-3191 (1981). Alternatively, automated synthesis may be preferred, for example, on an Applied Biosynthesis DNA synthesizer using cyanoethyl phosphoramidite chemistry. Preferably, the primers are chemically synthesized.

Suitable bases for preparing the oligonucleotide primers of the present invention may be selected from naturally occurring nucleotide bases such as adenine, cytosine, guanine, uracil, and thymine. It may also be selected from normaturally occurring or "synthetic" nucleotide bases such as 8-oxo-guanine, 6-mercaptoguanine, 4-acetylcytidine, 5-(carboxyhydroxyethyl) uridine, 2'-O-methylcytidine, 5-carboxymethylamino-methyl-2-thioridine, 5-carboxymethylaminomethyl uridine, dihydrouridine, 2'-O-methylpseudouridine, beta-D-galactosylqueosine, 2'-Omethylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, beta-D-mannosylqueosine, 5-methoxycarbonyl-methyluridine, 5-methoxyuridine, 2-methylthio-N6-isopentenyladenosine, N-((9-.beta.-D-ribofuranosyl-2-methylthiopurine-6-yl)carbamoyl)threonine, N-((9-beta-D-ribofuranosylpurine-6-yl) N-methylcarbamoyl) threonine, uridine-5-oxyacetic acid methylester, uridine-5-oxyacetic acid, wybutoxosine, pseudouridine, queosine, 2-thiocytidine, 5-methyl-2-thiouridine, 2-thiouridine, 2-thiouridine, 5-methyluridine, N-((9-beta-D-ribofuranosylpurine-6-yl) carbamoyl) threonine, 2'-O-methyl-5-methyluridine, 2'-O-methyluridine, wybutosine, and 3-(3-amino-3-carboxypropyl) uridine.

Likewise, chemical analogs of oligonucleotides (e.g., oligonucleotides in which the phosphodiester bonds have been modified, e.g., to the methylphosphonate, the phosphotriester, the phosphorothioate, the phosphorodithioate, or the phosphoramidate) may also be employed. Protection from degradation can be achieved by use of a "3'-end cap" strategy by which nuclease-resistant linkages are substituted for phosphodiester linkages at the 3' end of the oligonucleotide (Shaw et al., Nucleic Acids Res., 19:747 (1991)). Phosphoramidates, phosphorothioates, and methylphosphonate linkages all function adequately in this manner. More extensive modification of the phosphodiester backbone has been shown to impart stability and may allow for enhanced affinity and increased cellular permeation of oligonucleotides (Milligan et al., J. Med. Chem., 36:1923 (1993)). Many different chemical strategies have been employed to replace the entire phosphodiester backbone with novel linkages. Backbone analogues include phosphorothioate, phosphorodithioate, methylphosphonate, phosphoramidate, boranophosphate, phosphotriester, formacetal, 3'-thioformacetal, 5'-thioformacetal, 5'-thioether, carbonate, 5'-N-carbamate, sulfate, sulfonate, sulfamate, sulfonamide, sulfone, sulfite, sulfoxide, sulfide, hydroxylamine, methylene (methylimino) (MMI) or methyleneoxy (methylimino) (MOMI) linkages. Phosphorothioate and methylphosphonate-modified oligonucleotides are particularly preferred due to their availability through automated oligonucleotide synthesis. The oligonucleotide may be a "peptide nucleic acid" such as described by (Milligan et al., J. Med. Chem., 36:1923 (1993)). The only requirement is that the oligonucleotide primer should possess a sequence at least a portion of which is capable of binding to a portion of a target sequence.

The target polynucleotide may be double stranded or single stranded. In some embodiments, at least a portion of the single-stranded target polynucleotide is completely or substantially complementary to at least a portion of the oligonucleotide probe immobilized on the microarray. In other embodiments, the single-stranded target polynucleotide is completely complementary to the oligonucleotide probe immobilized on the microarray. FIG. 3 is a schematic drawing in accordance with the invention of microarray-based assay integrated with particles for the detection of luminophore-labeled double-stranded target polynucleotides.

Employing PCR, RT-PCR (for RNA molecules) or other methods, polynucleotide molecules/agents of interest can be converted to nucleic acid fragments and labeled with biotin, digoxin or the similar, which then binds with moieties on the surface of particles/beads. By coupling to the particles or beads, these nucleic acid fragments in solution are enriched. For double-stranded nucleic acid fragments, they are denatured to single-stranded ones. Beads are then coupled to specific microarray spots through target-probe hybridization, which directly or through further modifications, facilitate the detection of results with non-expensive devices or common commercial microarray scanners. Specific genes, SNPs or gene mutations, such as deletions, insertions, and indels, are thus identified. For SNPs/mutations, they are valuable for biomedical research and for developing pharmaceutical compounds or medical diagnostics. SNPs are also evolutionarily stable—not changing much from generation to generation—making them convenient to follow in population studies.

Any method may be used to assay the polynucleotide, that is, to determine the polymorphic sites, in this step of the invention. For example, any of the primer extension-based methods, ligase-based sequence determination methods, mismatch-based sequence determination methods, or microarray-based sequence determination methods described above may be used, in accordance with the present invention. Alternatively, such methods as restriction fragment length polymorphism (RFLP) detection, single strand conformation polymorphism detection (SSCP), denaturing gradient gel electrophoresis (DGGE), denaturing high-performance liquid chromatography (DHPLC), PCR-based assays such as the Taqman® PCR System (Applied Biosystems) may be used.

Allele-specific PCR (ASPCR) is known as amplification refractory mutation system (ARMS) or PCR-sequence specific primer (PCR-SSP), etc. With high accuracy, ASPCR is suitable for analyzing known SNPs/mutations in genetic sequences, which uses DNA polymerase without the 3'-5' exonuclease activity so that if the 3' end of a specific primer does not match the template, the primer can not be elongated and the PCR reaction is blocked. Utilizing multiplex PCR, multiple loci can be amplified simultaneously, and then distinguished by DNA microarray. The PCR amplification may be conducted in one tube, or in different tubes.

By employing the universal array technology, Tag sequences are conjugated with primers, and their final products can readily hybridize with the Tag probes. Microarrays here just serve as a decode tool. The Tag sequences are artificially designed and subject to critical filtering, they have the corresponding complementary sequences, cTag sequences. Each combination of Tag and cTag corresponds to an allele of a SNP/mutation in the target gene. The Tm difference between different Tag sequences equals or is less than 5° C., and the Tag sequences have no cross-hybridization among themselves or with the group of primers, have low homology to the species of the sample genomic DNA, and no hair-pin structures. Determination of genes or genotypes is based on the hybridization signal and the position of the Tag probes on microarray hybridized with the PCR products.

Figure 4:
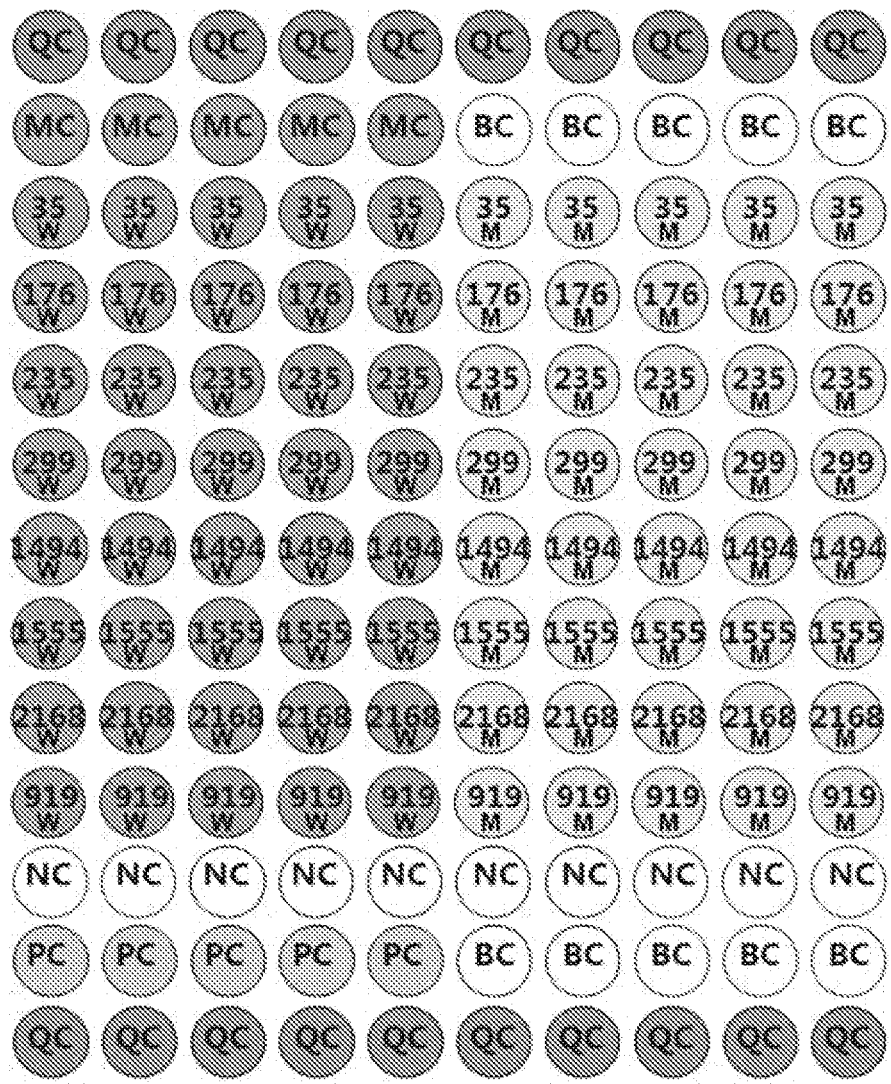
FIG. 4 is a layout of universal Tag array for de-multiplexing, corresponding to eight SNPs/mutations related to hereditary hearing loss. QC and BC represent positive and negative controls of spotting efficiency, respectively. PC and NC represent positive and negative controls of hybridization, respectively. MC represents positive control of the microsphere surface-modified moieties binding with their target molecules.

FIG. 4 shows the layout of universal Tag array as an example for de-multiplexing eight SNPs/mutations related to hereditary hearing loss, which only consists of 16 Tags with every Tag probe replicated horizontally for five consecutive ones. Each Tag probe on the universal array comprises a nucleotide sequence of any one of the Tag sequences shown in Table 1. In some variations, each Tag probe is 5'-amino-modified, and comprises a 15-nucleotide poly-dT spacer linked to the 5' end of the Tag sequences. QC and BC represent positive and negative controls of spotting efficiency, respectively. PC and NC represent positive and negative controls of hybridization, respectively. MC represents positive control of the microsphere surface-modified moieties binding with their targets. These considerations make sure that each step within assay procedure is accurately carried out as well as the final results. Of course, one can use many more or less Tag sequences with or without replicate spots for specific applications. These Tag sequences may be designed by methods of bioinformatics. Tag probes can also be derived from a biological species different from the species of the target gene. For example, if the species of the target is from human, the Tag sequences can be derived from sequences of bacteria. The Tag sequence is single stranded oligonucleotide or peptide oligonucleotide.

The universal array in this invention is different from the common microarray. For common microarray, the probes on the array may be gene-specific or allele-specific oligonucleotides. Different target gene panel or SNP/mutation panel needs different format of microarray. However, the universal array in this invention consists of Tag probes which are specifically designed, so they are not associated with allele-specific oligonucleotides or primers. The Tag sequences can be used as codes for different SNP/mutation of different genes or different species. One format of universal array can be used for detection of any gene or genotype. So such array is universal and the process of detection is a kind of de-coding step.

H. KITS

A kit useful for detecting a molecular interaction comprising a particle, a microarray and a probe molecule immobilized on the microarray is hereby provided in this invention. In certain aspect, the invention is also embodied in a kit comprising a universal Tag array. Preferably, the kit of the invention comprises set of primers for ASPCR amplification of a genetic information comprising two allele-specific primers and a common primer as set forth in Table 2. The kit of the invention may also comprise a polymerizing agent, for example, a thermostable nucleic acid polymerase such as those disclosed in U.S. Pat. Nos. 4,889,818; 6,077,664, and the like. The kit of the invention may also comprise chain elongating nucleotides, such as dATP, dTTP, dGTP, dCTP, and dITP, including analogs of dATP, dTTP, dGTP, dCTP and dITP, so long as such analogs are substrates for a thermostable nucleic acid polymerase and can be incorporated into a growing nucleic acid chain. In a preferred embodiment, the kit of the invention comprises at least one oligonucleotide primer pair, a polymerizing agent, and chain elongating nucleotides. The kit of the invention may optionally include buffers, vials, microtiter plates, and instructions for use.

I. EXEMPLARY EMBODIMENTS

The following examples are offered to illustrate but not to limit the invention.

Samples

Patient blood samples with known SNPs/mutations associated with hereditary deafness, and samples with unknown SNPs/mutations including buccal swabs and dried blood spots, were provided by Chinese PLA General Hospital.

Primers

Multiplex PCR primers used for analyzing a total of 8 SNPs/mutations are listed in Table 2. In column Mutation Type 'del' represents a deletion mutation, e.g., c.35delG means a deletion of G at position 35 in the coding region of GJB2; '>' represents a substitution mutation, e.g. c.2168A>G means a substitution of A by G at position 2168 in the coding region of SLC26A4 (PDS). Primer Name with 'WT' or 'MU' suffix represents an allele-specific primer capable of specifically amplifying the wild-type or mutant allele at the SNP/mutation locus, respectively. Primer Name with a 'RB' suffix represent a common primer, biotinylated at the 5'-termini, capable of amplifying both the wild-type allele and the mutant allele of the target genetic fragments including the SNP/mutation locus. The common primer is also fluorescence-labeled with Cy3-dTTP while synthesized, which is asterisked in Table 2. For each SNP/mutation locus the two allele-specific primers respectively pair with the common primer.

The universal array is a matrix made up of 16 Tag probes capable of hybridizing to the multiplex PCR products, besides positive quality control for sample spotting (QC), negative quality control for sample spotting (BC), positive quality control for hybridization (PC), negative quality control for hybridization (NC), and positive control of the streptavidin-coated particles binding with biotin-labeled DNA fragments (MC). QC is an oligonucleotide probe labeled with fluorescence HEX at one end and modified by an amino group ($NH_2$) at the other end to monitor the efficacy of sample spotting and fixing on the array. BC is a spotting buffer for quality control of cross contamination during sample spotting. NC is an oligonucleotide probe modified by an amino group which is theoretically incapable of hybridizing to any fragment in solution for quality control of nonspecific hybridization. PC is an oligonucleotide probe modified by an amino group which is capable of hybridizing to the house keeping gene products for quality control of PCR and hybridization. MC is an oligonucleotide probe modified by an amino group and biotinylated for quality control of the streptavidin-coated particles binding with biotinylated DNA fragments.

The Tag probes on the universal array are designed according to the format: $NH_2$-TTTTTTTTTTTTTTT-TagX, where X is a natural number between 1 and 16. The Tag probes have a 5'-amino group modification, followed by poly-dT15, followed by Tag1 to Tag18 with the sequences 1 to 16 listed in Table 1, respectively. The nucleotide sequences of Tag1 to Tag16 in the Tag probes are identical to the corresponding sequences of Tag1 to Tag16 of the primers, respectively.

Multiplex Allele-Specific PCR

Multiplex PCR was carried out using the genomic DNA extracted from whole blood samples, buccal swabs and dried blood spots from patients or high risk family for deafness as templates. Reaction volumes were 20 µL, and contained 0.2 mM dNTPs, 1×Qiagen PCR buffer, with addition of $MgCl_2$ to 2 mM, 1 unit of HotStartTaq DNA polymerase lacking of a 3' to 5' exonuclease activity (Qiagen, Hilden, Germany) and 10 ng of genomic DNA, and 0.2 µM primers for each selected SNP/mutation. For determining the assay detection limit, different quantities of genomic DNA were used, ranging from 5 ng to 100 ng. Amplification was performed in a PTC-225 Thermal Cycler (MJ Research, Watertown, Mass.). Amplification program was as follows: first 95° C. for 15 min; then 94° C. for 30 seconds, ramp at 0.5° C./second down to 55° C., hold at 55° C. for 30 seconds, ramp at 0.2° C./second up to 70° C., hold at 60° C. for 45 seconds, repeat for 10 cycles; and then 90° C. for 30 seconds, ramp at 0.5° C./second down to 55° C., hold at 55° C. for 30 seconds, ramp at 0.2° C./second up to 70° C., hold at 70° C. for 45 seconds, repeat for 22 cycles; finally hold at 60° C. for 10 minutes; and 4° C. soak.

Single-Stranded DNA Isolation

Streptavidin-coated MyOne Dynal beads (Invitrogen Dynal AS, Oslo, Norway) were used, which could capture the biotin-labeled PCR products. These beads were first pretreated according to the protocol from the supplier, and 3 µL of beads were added to 5 µL PCR products, incubating for 10 minutes. Then two washes with binding and washing buffer (5 mM Tris-HCl pH 7.5, 0.5 mM EDTA, 1 M NaCl) were followed. Alkaline denaturation was performed twice with 60 µL freshly prepared 0.1 N NaOH for 10 minutes each time. After that, 15 µL hybridization buffer (9×SSC, 7.5×Denhardt's, 37.5% (v/v) Formamide, 0.15% SDS) was added.

Universal Array Hybridization

The hybridization mixture was added to the surface of universal Tag array. The slides were incubated at 50° C. for 1 hour and washed 2 minutes each at room temperature in two types of washing solutions (Type I: 1×PBS and 0.2% Tween-20; Type II: 0.03×SSC). If magnetic forces are employed to manipulate paramagnetic particles or beads, duration of 30 minutes was used for hybridization. Finally, the slides were dried by centrifugation. The slides were scanned with a confocal LuxScan 10K scanner (CapitalBio, Beijing, China), and the data of obtained images were extracted with SpotData software (CapitalBio) for further analysis. Laser power and photomultiplier tube (PMT) index were 70% and 700, respectively.

Example 1

Multiplexed Analysis of SNPs/Mutations Related to Hereditary Hearing Loss

Microarray-based assay integrated with paramagnetic microspheres was used for multiplexed analysis of SNPs/mutations related to hereditary hearing loss. Commercial fluorescent scanner was employed to detect the results, which were accomplished by enriching multiple PCR products with microspheres, harvesting ssDNA fragments, coupling microspheres to universal Tag array through hybridization, and decoding them with the universal Tag array.

FIG. 4 shows, as an example, the layout of universal Tag array corresponding to eight SNPs/mutations related to hereditary hearing loss, where SNPs/mutations in GJB2 (Cx26) gene, SLC26A4 (PDS) gene, and 12S rRNA (MTRNR1) gene were selected. Name with 'W' or 'M' suffix represents the probe corresponding to the wild-type or mutant allele at the SNP/mutation locus, respectively. On the left of the array are probes for wild-type alleles, on the right are probes for mutant alleles, and each probe is printed horizontally as five replica spots. For detecting c.35delG, c.176_191del16, c.235delC, and c.299_300delAT in the GJB2 (Cx26) gene, c.2168A>G and c.919-2A>G (IVS7-2A>G) in the SLC26A4 (PDS) gene, and m.1494C>T and m.1555A>G in 12S rRNA gene (MTRNR1, belonging to mitochondria gene), the primers for each SNP/mutation may include two allele-specific primers and one common primer labeled with biotin as well as Cy3, as shown in Table 2. Each allele-specific primer comprises a unique Tag sequence linked to the 5' end of a nucleotide sequence which is identical or complementary to a target gene sequence containing the SNP/mutation locus. And each allele-specific primer along with common primer generates a DNA fragment containing the SNP/mutation locus through PCR amplifications. The probes comprising sequences identical to their corresponding Tag sequences in allele-specific primers are immobilized on a solid surface to form the universal array. Streptavidin-coated particles can be used to capture biotin-labeled DNA products, and after harvesting of ssDNAs the target-probe hybridization is carried out. The results can be interrogated by the fluorencence intensity of coupled particles and the position of corresponding Tag probe on the array.

Figure 5:
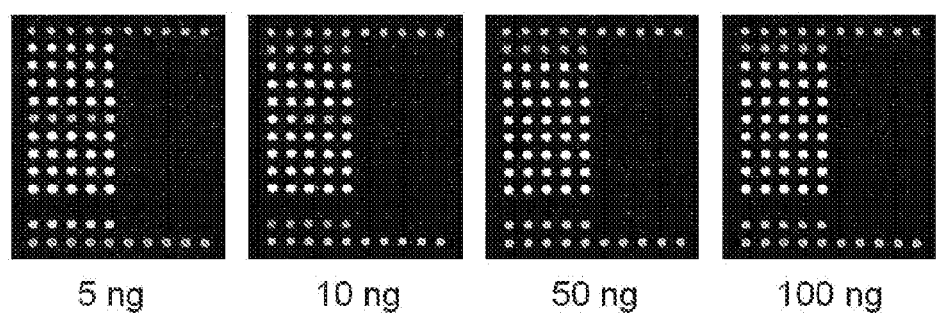
FIG. 5 shows the results of detection limit evaluation using a patient sample with all wild-type alleles for eight selected SNPs/mutations related to hereditary hearing loss, using universal Tag array-based assay integrated with microparticles or microspheres.

To determine the assay detection limit, different quantities of genomic DNA from clinical samples, with all wild-type alleles at nine selected SNP/mutation loci, were used, ranging from 5 ng to 100 ng. As shown in FIG. 5, eight selected SNPs/mutations related to hereditary hearing loss were simultaneously analyzed, and according to the layout of the universal Tag array schemed in FIG. 4, all the wild-type-specific probes on the left of the array showed positive signal while almost no hybridization signal was detected from mutant-specific probes on the right, indicating that the current detection limit of this application of the invention was 5 ng of genomic DNA.

Figure 6:
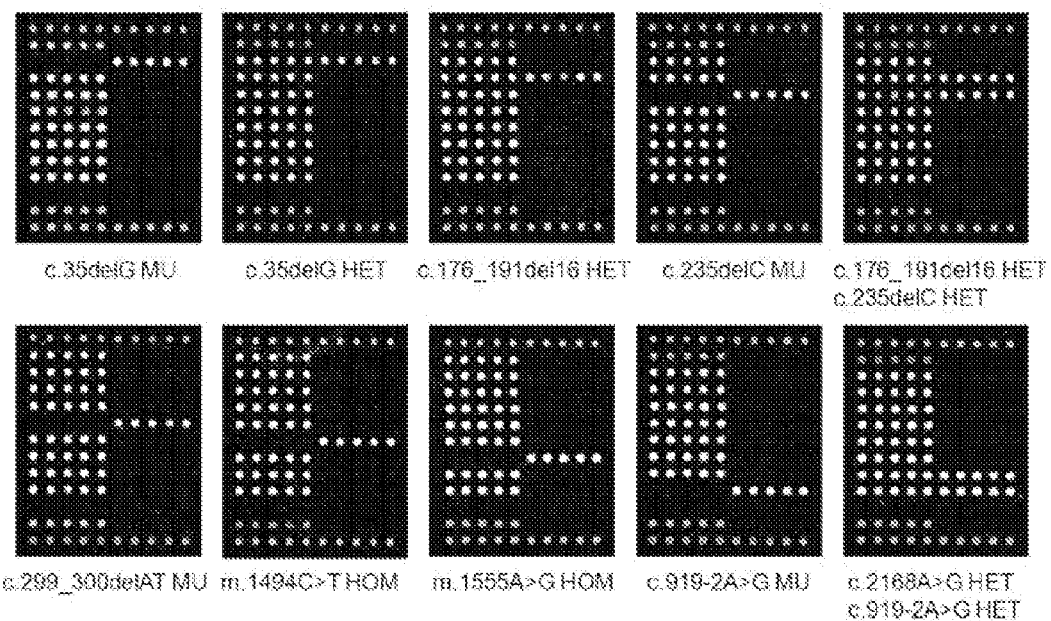
FIG. 6 shows the assay results with patient samples that contain at least one mutant allele for eight selected SNPs/mutations related to hereditary hearing loss, using universal Tag array-based assay integrated with microparticles or microspheres.

Besides the wild-type, mutant alleles related to eight selected SNPs/mutations from homozygous and heterozygous clinical samples were examined, as shown in FIG. 6. Within the range from 5 ng to 100 ng, any amount of genomic DNA was suitable for this assay. 'MU' and 'HET' suffix represent the homozygote and heterozygote, respectively. For heterozygous samples, they contain both wild-type and mutant alleles at a SNP/mutation site. For the SNP/mutation sites in the mitochondria genes such as m.1555A>G, 'HOM' and 'HET' suffix represent homoplasmic and heteroplasmic mutation state, respectively. With the confirmation of other genotyping methods such as DNA sequencing, the results were of 100% accuracy, demonstrating that such platform had high specificity and was capable of genotyping clinical samples. With the extremely high sensitivity of this genotyping platform, one also can apply it to detect rare samples. In practice, buccal swabs and dried blood spots from families affected by deafness were collected, and their assay results were 100% correct, as confirmed by DNA sequencing. The successful genotyping paves the way for this genotyping platform widely applied in genetic and diagnostic analysis associated with a large number of diseases as well as their corresponding SNPs/mutations.

TABLE 1

The Probes of the Universal Tag Array

| Name | Sequence (5'->3') | SEQ ID NO. |
|---|---|---|
| Tag-1 | $NH_2$-$T_{15}$-GAGGAGATCGTAGCTGGTGCAT | (SEQ ID NO: 1) |
| Tag-2 | $NH_2$-$T_{15}$-TCGCTGCCAACCGAGAATTGCA | (SEQ ID NO: 2) |
| Tag-3 | $NH_2$-$T_{15}$-GAGCAAGCGCAAACGCAGTACT | (SEQ ID NO: 3) |
| Tag-4 | $NH_2$-$T_{15}$-GCATAGACGTGGCTCAACTGTC | (SEQ ID NO: 4) |
| Tag-5 | $NH_2$-$T_{15}$-CAAGGCACGTCCCAGACGCATCAA | (SEQ ID NO: 5) |
| Tag-6 | $NH_2$-$T_{15}$-TCGGCACGCGCGAGATCACCATC | (SEQ ID NO: 6) |
| Tag-7 | $NH_2$-$T_{15}$-TTTTCCCGTCCGTCATCGCTCAAG | (SEQ ID NO: 7) |
| Tag-8 | $NH_2$-$T_{15}$-GGTATCGCGACCGCATCCCAATCT | (SEQ ID NO: 8) |
| Tag-9 | $NH_2$-$T_{15}$-TCCCTGTCTCGTTGCGTGTCTCGT | (SEQ ID NO: 9) |
| Tag-10 | $NH_2$-$T_{15}$-GTTAGGGTCGCGCCAAACTCTCC | (SEQ ID NO: 10) |
| Tag-11 | $NH_2$-$T_{15}$-AGCTAGACCACTCAGCAGACTG | (SEQ ID NO: 11) |
| Tag-12 | $NH_2$-$T_{15}$-CGCCTTAGACAGCTTGCTCATG | (SEQ ID NO: 12) |
| Tag-13 | $NH_2$-$T_{15}$-ACCTTTCGCTTCACCGGCCGATC | (SEQ ID NO: 13) |
| Tag-14 | $NH_2$-$T_{15}$-GCTCGAAGAGGCGCTACAGATCC | (SEQ ID NO: 14) |
| Tag-15 | $NH_2$-$T_{15}$-CTGTTAAACGTCAGAGCGCAGC | (SEQ ID NO: 15) |
| Tag-16 | $NH_2$-$T_{15}$-AGTCGAAGTGTGCGTCAGACTC | (SEQ ID NO: 16) |
| MC | $NH_2$-$T_{15}$-GCAACCACCACCGGAGG-Biotin | (SEQ ID NO: 17) |
| PC | $NH_2$-$T_{15}$-TGCACGAGTTGGGTGAGTTTGG | (SEQ ID NO: 18) |
| NC | $NH_2$-$T_{15}$-GCTTTATCCCTAACGTCATCGGG | (SEQ ID NO: 19) |
| QC | $NH_2$-$T_{15}$-CAGAGTGCTTGGTGCCATAAC-HEX | (SEQ ID NO: 20) |

TABLE 2

SNPs/Mutations and Their Specially Designed Primers

| Mutation Type | Primer Name | Primer Sequence (5'->3') | SEQ ID NO. |
|---|---|---|---|
| c.35delG | t35delG-WT | Tag1-TGTTTGTTCACACCCCCGAG | (SEQ ID NO: 21) |
|  | t35delG-MU | Tag2-TGTTTGTTCACACCCGCAG | (SEQ ID NO: 22) |
|  | 35delG-RB | Biotin-GCAT*GCTTGCTTACCCAGAC | (SEQ ID NO: 23) |
| c.176_191del16 | t176_191del16-WT | Tag3-CCAGGCTGCAAGAACGTGTG | (SEQ ID NO: 24) |
|  | t176_191del16-MU | Tag4-ACCCTGCAGCCAGCTACG | (SEQ ID NO: 25) |
|  | 176_191del16-RB | Biotin-GAGCCT*TCGATGCGGACC | (SEQ ID NO: 26) |

TABLE 2-continued

SNPs/Mutations and Their Specially Designed Primers

| Mutation Type | Primer Name | Primer Sequence (5'->3') | SEQ ID NO. |
|---|---|---|---|
| c.235delC | t235delC-WT | Tag5-AAACGGCTATGGGCCCTG | (SEQ ID NO: 27) |
| | t235delC-MU | Tag6-ATCCGGCTATGGGCCTG | (SEQ ID NO: 28) |
| | 235delC-RB | Biotin-GAGCCT*TCGATGCGGACC | (SEQ ID NO: 29) |
| c.299_300delAT | t299-300delAT-WT | Tag7-TGGCCTACCGGAGACATGA | (SEQ ID NO: 30) |
| | t299-300delAT-MU | Tag8-CGTGGCCTACCGGAGACGA | (SEQ ID NO: 31) |
| | 299-300delAT-RB | Biotin-GAGCCT*TCGATGCGGACC | (SEQ ID NO: 32) |
| c.2168A>G | t2168A>G-WT | Tag9-GACACATTCTTTATGACGGTCCA | (SEQ ID NO: 33) |
| | t2168A>G-MU | Tag10-ACATTCTTTTGTCGGTCCG | (SEQ ID NO: 34) |
| | 2168A>G-RB | Biotin-CAAGGT*TTTCCAGATTGCTGAG | (SEQ ID NO: 35) |
| c.919-2A>G | t919-2A>G-WT | Tag11-AATGGCAGTAGCAATTATCGACT | (SEQ ID NO: 36) |
| | t919-2A>G-MU | Tag12-TGGCAGTAGCAATTATCGTGC | (SEQ ID NO: 37) |
| | 919-2A>G-RB | Biotin-CGTGT*AGCAGCAGGAAGTAT | (SEQ ID NO: 38) |
| m.1494C>T | t1494C>T-WT | Tag13-CTTTGAAAGTATACTTGAGGAGG | (SEQ ID NO: 39) |
| | t1494C>T-MU | Tag14-CTTTGAAGTATACTTGAGGAGA | (SEQ ID NO: 40) |
| | 1494C>T-RB | Biotin-CCCT*GATGAAGGCTACAAAG | (SEQ ID NO: 41) |
| m.1555A>G | t1555A>G-WT | Tag15-ACTTACCATGTTACGACTAGT | (SEQ ID NO: 42) |
| | t1555A>G-MU | Tag16-CACTTACCATGTTACGACTCGC | (SEQ ID NO: 43) |
| | 1555A>G-RB | Biotin-CCCT*GATGAAGGCTACAAAG | (SEQ ID NO: 44) |
| | PC-F | PC-GTGGACTGCTACATTGGCC | (SEQ ID NO: 45) |
| | PC-R | Biotin-TCGAGGCT*TGTCCTTGTGC | (SEQ ID NO: 46) |

What is claimed is:

1. A method for detecting a target molecule using a microarray, which method comprises:
   a) labeling the target molecule with a luminophore;
   b) coupling the target molecule to a particle;
   c) binding the target molecule that is labeled with the luminophore and coupled to the particle, to a probe molecule immobilized on the microarray; and
   d) detecting the interaction between the target molecule and the probe molecule,
   wherein the target molecule is a polynucleotide,
   wherein the method further comprises before the detecting step a step of amplifying the target polynucleotide, and
   wherein the target polynucleotide is amplified using a primer comprising a sequence as set forth in Table 2.

2. The method of claim 1, wherein the particle is a microparticle having a diameter of between about 0.01 μm and about 1000 μm.

3. The method of claim 1, wherein the particle is coated with a functional group or moiety selected from the group consisting of a chemical group, a polynucleotide, a polypeptide, an antibody, a small molecule compound, a peptide, and a carbohydrate.

4. The method of claim 3, wherein the target molecule is modified and the target molecule is coupled to the particle through an interaction between the modification of the target molecule and the functional group or moiety on the particle.

5. The method of claim 1, wherein the probe molecule is selected from the group consisting of a polynucleotide, a polypeptide, an antibody, a small molecule compound, a peptide, and a carbohydrate.

6. The method of claim 1, wherein the luminophore is selected from the group consisting of a fluorophore, a phosphor, and a chromophore.

7. The method of claim 1, wherein the probe molecule forms a spot on the microarray, wherein the spot is between about 0.01 mm and about 5 mm in diameter.

8. The method of claim 1, wherein the interaction in step d) is detected by visualizing the particle on the spot under a visible light and/or using fluorescence scanning.

9. The method of claim 1, wherein the target molecule comprises genetic information associated with hereditary hearing loss, wherein the genetic information is within a target gene of GJB2 (Cx26), SLC26A4 (PDS), or 12S rRNA (MTRNR1).

10. A method for detecting a target molecule using a microarray, which method comprises:
    a) labeling the target molecule with a luminophore;
    b) coupling the target molecule to a particle;
    c) binding the target molecule that is labeled with the luminophore and coupled to the particle, to a probe molecule immobilized on the microarray; and
    d) detecting the interaction between the target molecule and the probe molecule,
    wherein the target molecule is a polynucleotide,
    wherein the method further comprises before the detecting step a step of amplifying the target polynucleotide, and
    wherein the target polynucleotide is amplified using at least two allele-specific primers and their corresponding common primer as set forth in Table 2.

11. The method of claim 10, wherein the particle is a microparticle having a diameter of between about 0.01 μm and about 1000 μm.

12. The method of claim 10, wherein the particle is coated with a functional group or moiety selected from the group consisting of a chemical group, a polynucleotide, a polypeptide, an antibody, a small molecule compound, a peptide, and a carbohydrate.

13. The method of claim 12, wherein the target molecule is modified and the target molecule is coupled to the particle through an interaction between the modification of the target molecule and the functional group or moiety on the particle.

14. The method of claim 10, wherein the probe molecule is selected from the group consisting of a polynucleotide, a polypeptide, an antibody, a small molecule compound, a peptide, and a carbohydrate.

15. The method of claim 10, wherein the luminophore is selected from the group consisting of a fluorophore, a phosphor, and a chromophore.

16. The method of claim 10, wherein the probe molecule forms a spot on the microarray, wherein the spot is between about 0.01 mm and about 5 mm in diameter.

17. The method of claim 10, wherein the interaction in step d) is detected by visualizing the particle on the spot under a visible light and/or using fluorescence scanning.

18. The method of claim 10, wherein the target molecule comprises genetic information associated with hereditary hearing loss, wherein the genetic information is within a target gene of GJB2 (Cx26), SLC26A4 (PDS), or 12S rRNA (MTRNR1).

19. A method for detecting a target molecule using a microarray, which method comprises:
    a) labeling the target molecule with a luminophore;
    b) coupling the target molecule to a particle;
    c) binding the target molecule that is labeled with the luminophore and coupled to the particle, to a probe molecule immobilized on the microarray; and
    d) detecting the interaction between the target molecule and the probe molecule,
    wherein the target molecule is selected from the group consisting of a polynucleotide, a polypeptide, an antibody, a small molecule compound, a peptide and a carbohydrate,
    wherein the microarray comprises a universal tag array, and
    wherein the universal tag array comprises at least two of the Tag sequences as set forth in Table 1.

20. The method of claim 19, wherein the particle is a microparticle having a diameter of between about 0.01 μm and about 1000 μm.

21. The method of claim 19, wherein the particle is coated with a functional group or moiety selected from the group consisting of a chemical group, a polynucleotide, a polypeptide, an antibody, a small molecule compound, a peptide, and a carbohydrate.

22. The method of claim 21, wherein the target molecule is modified and the target molecule is coupled to the particle through an interaction between the modification of the target molecule and the functional group or moiety on the particle.

23. The method of claim 19, wherein the probe molecule is selected from the group consisting of a polynucleotide, a polypeptide, an antibody, a small molecule compound, a peptide, and a carbohydrate.

24. The method of claim 19, wherein the luminophore is selected from the group consisting of a fluorophore, a phosphor, and a chromophore.

25. The method of claim 19, wherein the probe molecule forms a spot on the microarray, wherein the spot is between about 0.01 mm and about 5 mm in diameter.

26. The method of claim 19, wherein the interaction in step d) is detected by visualizing the particle on the spot under a visible light and/or using fluorescence scanning.

27. The method of claim 19, wherein the target molecule comprises genetic information associated with hereditary hearing loss, wherein the genetic information is within a target gene of GJB2 (Cx26), SLC26A4 (PDS), or 12S rRNA (MTRNR1).

\* \* \* \* \*